US011521720B2

(12) United States Patent
Boyd et al.

(10) Patent No.: US 11,521,720 B2
(45) Date of Patent: Dec. 6, 2022

(54) USER MEDICAL RECORD TRANSPORT USING MOBILE IDENTIFICATION CREDENTIAL

(71) Applicant: The Government of the United States of America, as represented by the Secretary of Homeland Security, Washington, DC (US)

(72) Inventors: Daniel A. Boyd, Arlington, VA (US); Kelli L. Biegger, McLean, VA (US); Chang Ellison, Arlington, VA (US); Brandon P. Gutierrez, Burke, VA (US); Jason Lim, Alexandria, VA (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 0 days.

(21) Appl. No.: 17/167,874

(22) Filed: Feb. 4, 2021

(65) Prior Publication Data

US 2021/0319862 A1    Oct. 14, 2021

Related U.S. Application Data

(60) Provisional application No. 63/009,175, filed on Apr. 13, 2020.

(51) Int. Cl.
*G16H 10/60* (2018.01)
*G06F 21/62* (2013.01)
(Continued)

(52) U.S. Cl.
CPC .......... *G16H 10/60* (2018.01); *G06F 21/31* (2013.01); *G06F 21/62* (2013.01); *G16H 15/00* (2018.01)

(58) Field of Classification Search
None
See application file for complete search history.

(56) References Cited

U.S. PATENT DOCUMENTS 7,849,501 B2   12/2010 Vishik et al.
8,353,016 B1   1/2013 Pravetz et al.
(Continued)

OTHER PUBLICATIONS

Carnley, P. Renee, et al., "Trusted Digital Identities for Mobile Devices", 2020 IEEE Intl Conf on Dependable, Autonomic and Secure Computing, Intl Conf on Pervasive Intelligence and Computing,Intl Conf on Cloud and Big Data Computing, Intl Conf on Cyber Science and Technology Congress, (DASC/PiCom/CBDCom/CyberSciTech) (pp. 483-490), Aug. 1, 2020.

*Primary Examiner* — Thu N Nguyen
(74) *Attorney, Agent, or Firm* — Lavanya Ratnam; Robert W. Busby; William Washington

(57) ABSTRACT

In an example, a patient using a user mobile-identification-credential device (UMD) requests the patient's medical record from a medical office using a relying party system (RPS). The RPS requests identification information of the patient from the UMD and receives, based on consent of the patient, some or all patient identification information associated with a mobile identification credential (MIC) previously provisioned to the UMD an authorizing party system (APS). The RPS receives verification of the received patient identification information, uses the verified user ID information to verify or not verify the identity of the patient, and verifies the identity of the patient before granting the request to provide the medical record to the patient. The patient has the option of releasing part or all of the medical record to a third party. In one embodiment, the patient stores the medical record with a service provider and authorizes, in advance, certain medical personnel to have access to it.

22 Claims, 14 Drawing Sheets

(51) Int. Cl.
*G06F 21/31* (2013.01)
*G16H 15/00* (2018.01)

(56) References Cited

U.S. PATENT DOCUMENTS

| | | |
|---|---|---|
| 9,147,117 B1 | 9/2015 | Madhu et al. |
| 10,503,912 B1 | 12/2019 | Kerr |
| 2007/0079136 A1 | 4/2007 | Vishik et al. |
| 2010/0063830 A1* | 3/2010 | Kenedy ................. G16H 50/70 705/2 |
| 2012/0144461 A1 | 6/2012 | Rathbun |
| 2014/0020073 A1 | 1/2014 | Ronda et al. |
| 2014/0129255 A1* | 5/2014 | Woodson ............... G16H 10/60 705/3 |
| 2014/0207537 A1 | 7/2014 | Joyce et al. |
| 2016/0055322 A1 | 2/2016 | Thomas |
| 2016/0078581 A1 | 3/2016 | Maher |
| 2017/0032485 A1 | 2/2017 | Vemury |
| 2017/0069151 A1 | 3/2017 | Saravanan |
| 2017/0094514 A1 | 3/2017 | Kelts et al. |
| 2018/0012324 A1* | 1/2018 | Kelts ................... G06Q 30/018 |
| 2018/0165655 A1 | 6/2018 | Marcelle et al. |
| 2018/0166160 A1 | 6/2018 | Walton, III |
| 2019/0036688 A1* | 1/2019 | Wasily ................ H04L 63/0823 |
| 2019/0043148 A1 | 2/2019 | Vemury |
| 2019/0057412 A1 | 2/2019 | Bhattacharjee et al. |
| 2019/0057763 A1* | 2/2019 | Stockert .................. G06F 21/30 |
| 2019/0163876 A1 | 5/2019 | Remme et al. |
| 2019/0164165 A1 | 5/2019 | Ithabathula |
| 2019/0287111 A1 | 9/2019 | Cvetkovich et al. |
| 2020/0043579 A1* | 2/2020 | McEwing .............. G16H 10/60 |
| 2020/0168306 A1* | 5/2020 | Chen ....................... H04L 63/12 |

* cited by examiner

USER MEDICAL RECORD TRANSPORT USING MOBILE IDENTIFICATION CREDENTIAL

CROSS-REFERENCE TO RELATED APPLICATIONS

The application claims the benefit of priority from U.S. Provisional Patent Application No. 63/009,175, filed on Apr. 13, 2020, entitled USER MEDICAL RECORD TRANSPORT USING MOBILE IDENTIFICATION CREDENTIAL, the disclosure of which is incorporated by reference in its entirety.

STATEMENT OF GOVERNMENT INTEREST

The present invention was made by employees of the United States Department of Homeland Security in the performance of their official duties. The U.S. Government has certain rights in this invention.

FIELD

The discussion below relates generally to systems and methods of verifying the identity of a patient before providing the patient's medical record to the patient's device for transport and, more specifically, to verifications that make use of mobile identification credentials.

BACKGROUND

Verifying a patient's identity before releasing the patient's medical record is of utmost importance because protecting patient privacy and maintaining confidentiality of the patient's medical record is a top priority for many if not all patients.

Briefly, the patient wishes to obtain his or her medical record from a medical office for any of a variety of reasons. Doing so in person has previously required showing one or two forms of identification cards and is conventionally considered most reliable in protecting privacy and confidentiality. Identity verification performed in person is not foolproof, however. False verification can occur due to human error or carelessness or fraud. More recently, a medical office allows a patient to sign in electronically to a password-protected account and obtain the medical record. The drawback is that the account can be hacked, or it can be accessed by another person using a stolen password or by taking advantage of the carelessness of the patient.

SUMMARY

Embodiments of the present disclosure are directed to apparatuses and methods for providing a robust and secure way for a medical establishment or entity (e.g., hospital, medical office, medical facility, or the like) to verify the identity of a patient by leveraging a mobile identification credential (MIC) before providing the patient's medical record to the patient's device for transport. An example enables convenient downloading of the medical record by the patient making the request in person according to an embodiment, or electronically from a remote location according to another embodiment. In some embodiments, the risk of a breach of the confidentiality of the patient's medical record is reduced by virtue of the trust that accompanies use of the MIC. These embodiments establish trust that the medical record is provided to the proper person. The experience of the patient is enhanced, and specific embodiments support easier download or transfer of his or her medical record from one medical entity, transport of the medical record, and upload or transfer of it to another medical entity (e.g., another hospital or medical office, prospective or current employer, insurance company, an opposing party or the court in a litigation, etc.). As used herein, medical record encompasses all healthcare-related information (including dental care, vision care, physical therapy, psychological care, etc.). Here, the example of medical records and medical entities illuminates the discussion but is not intended to limit the scope; other, regulated situations that involve providing data or information to a user or involve accepting the same from a user are included. In this disclosure, "user" and "patient" are used interchangeably to refer to the MIC user as a patient in the medical records context.

In one embodiment, the patient makes a request for his or her medical record in person at a medical office. The patient presents a user mobile-identification-credential device (UMD) that includes MIC such as a mobile driver's license (mDL) as part of an environment that supports MICs. In such an environment, the MIC is issued by an Authorizing Party AP), such as a state department of motor vehicles (DMV) or some other issuing authority, using an Authorizing Party System (APS). The UMD interacts with another device to share some or all of the content of the MIC. The device that is to receive the MIC information is held by the medical office, which is a relying party (RP) that will rely on the information yielded via the MIC. The device of the relying party is referred to as a Relying Party System (RPS). Upon verifying the identity of the patient, the requested medical record is released by the RPS to the patient. In another embodiment, the request may be made from a remote location via a network. In that case, an additional liveness check may be typically used to ensure the request is made by the patient matching the MIC.

In another embodiment, the patient releases medical records to a third party. For example, the patient may be an employee of an employer. The employer requires verification that the employee has a medical condition requiring accommodation. The patient/employee, in one embodiment, obtains his or her medical record from a medical office and releases it to the employer. In another embodiment, the patient/employee releases the medical record from the medical office to the employer.

In another embodiment, the patient releases a medical record, linked to a MIC, to a government entity. For example, the patient may be a traveler. The government requires verification from the traveler that the traveler has a medical record containing information that the traveler has an immunity to a contagion or has received a specific vaccine, in order to allow the traveler to travel (pass through a government-controlled barrier to entry). The traveler, in one embodiment, obtains his or her medical record from a medical office after the medical record is released to the requestor based on the identity asserted from a provided MIC, and may release both the MIC (as verification of identity) and the requisite medical record (as verification of infection status) to the government. In another embodiment, the traveler authorizes the release of the medical record directly from the medical record holder to the government after using the MIC to assert ownership (through identity) of the medical record.

In another embodiment, as an example, a certificate of immunity for COVID-19 immunity would be layered as an attribute to the underlying mobile digital identity on the traveler's device. Upon presentation of the mobile identity to the government, the certificate of immunity for COVID-19 associated to the underlying and validated identity would also be released to the government that can be separately validated via a cryptographic mechanism that can be authenticated directly with the certificate issuing government authority.

An aspect of the present disclosure is directed to a method for a patient having a patient device to request a medical record of the patient from a medical office having a medical office system. The method comprises: receiving, by the medical office system from the patient device, a request for the medical record; sending, by the medical office system to the patient device, a request for identification information of the patient; receiving, by the medical office system, part or all of patient information associated with a first MIC which the patient device received from a first authorizing party system (APS), wherein the patient has consented to release the part or all of patient information to the medical office system, and wherein the part or all of patient information has been verified; using, by the medical office system, the verified part or all of patient information associated with the first MIC to verify or not verify the identity of the patient; and verifying the identity of the patient, by the medical office system, before granting the request to provide the medical record to the patient.

In accordance with another aspect of the disclosure, a medical office system for processing a request for a medical record from a patient device of a patient, the medical office system comprising a computer programmed to: receive, from the patient device, a request for the medical record; send, to the patient device, a request for identification information of the patient; receive part or all of patient information associated with a first MIC which the patient device received from a first authorizing party system (APS), wherein the patient has consented to release the part or all of patient information to the medical office system, and wherein the part or all of patient information has been verified; use the verified part or all of patient information associated with the first MIC to verify or not verify the identity of the patient; and verify the identity of the patient before granting the request to provide the medical record to the patient.

Another aspect of this disclosure is directed to a system, comprising a patient device and a medical office system of a medical office, for a patient using the patient device to request a medical record of the patient from the medical office system of the medical office, the medical office system including a medical office computer programmed to perform operations according to medical office instructions, the patient device including a patient computer programmed to perform operations according to patient instructions, the patient device having received a first MIC from a first authorizing party system (APS), the first APS including an APS computer programmed to perform operations according to APS instructions. The patient device sends, to the medical office system, a request for providing the medical record to the patient. The medical office system sends, to the patient device, a request for identification information of the patient. The patient device receives, from the patient, consent to release part or all of patient information associated with the first MIC. Either (i) the patient device sends, to the medical office system, the consented part or all of patient information, and the first APS verifies the part or all of patient information associated with the first MIC or (ii) the first APS sends, to the medical office system, the consented part or all of patient information as verified part or all of patient information associated with the first MIC. The medical office system uses the verified part or all of patient information associated with the first MIC to verify or not verify the identity of the patient. The medical office system verifies the identity of the patient before granting the request to provide the medical record to the patient.

Yet another aspect of the disclosure is directed to a system, comprising a medical personnel system and a service provider system of a service provider, for medical personnel using the medical personnel system to request a medical record of a patient from the service provider system of the service provider, the service provider system including a service provider computer programmed to perform operations according to service provider instructions, the medical personnel system including a medical personnel computer programmed to perform operations according to medical personnel instructions, the medical personnel computer having received a first mobile identification credential (MIC) from a first authorizing party system (APS), the first APS including an APS computer programmed to perform operations according to APS instructions. The medical personnel system sends, to the service provider system, a request for providing the medical record of the patient to the medical personnel. The service provider system sends, to the medical personnel system, a request for identification information of the medical personnel. The medical personnel system receives, from the medical personnel, consent to release part or all of medical personnel information associated with the first MIC. Either (i) the medical personnel system sends, to the service provider system, the consented part or all of medical personnel information, and the first APS verifying the part or all of medical personnel information associated with the first MIC or (ii) the first APS sends, to the service provider system, the consented part or all of medical personnel information as verified part or all of medical personnel information associated with the first MIC. The service provider system uses the verified part or all of medical personnel information associated with the first MIC to verify or not verify the identity of the medical personnel. The service provider system verifies the identity of the medical personnel before granting the request to provide the medical record of the patient to the medical personnel.

Other features and aspects of various embodiments will become apparent to those of ordinary skill in the art from the following detailed description which discloses, in conjunction with the accompanying drawings, examples that explain features in accordance with embodiments. This summary is not intended to identify key or essential features, nor is it intended to limit the scope of the invention, which is defined solely by the claims.

BRIEF DESCRIPTION OF THE DRAWINGS

The attached drawings help explain the embodiments described below.

DETAILED DESCRIPTION

System Embodiments

Figure 1:
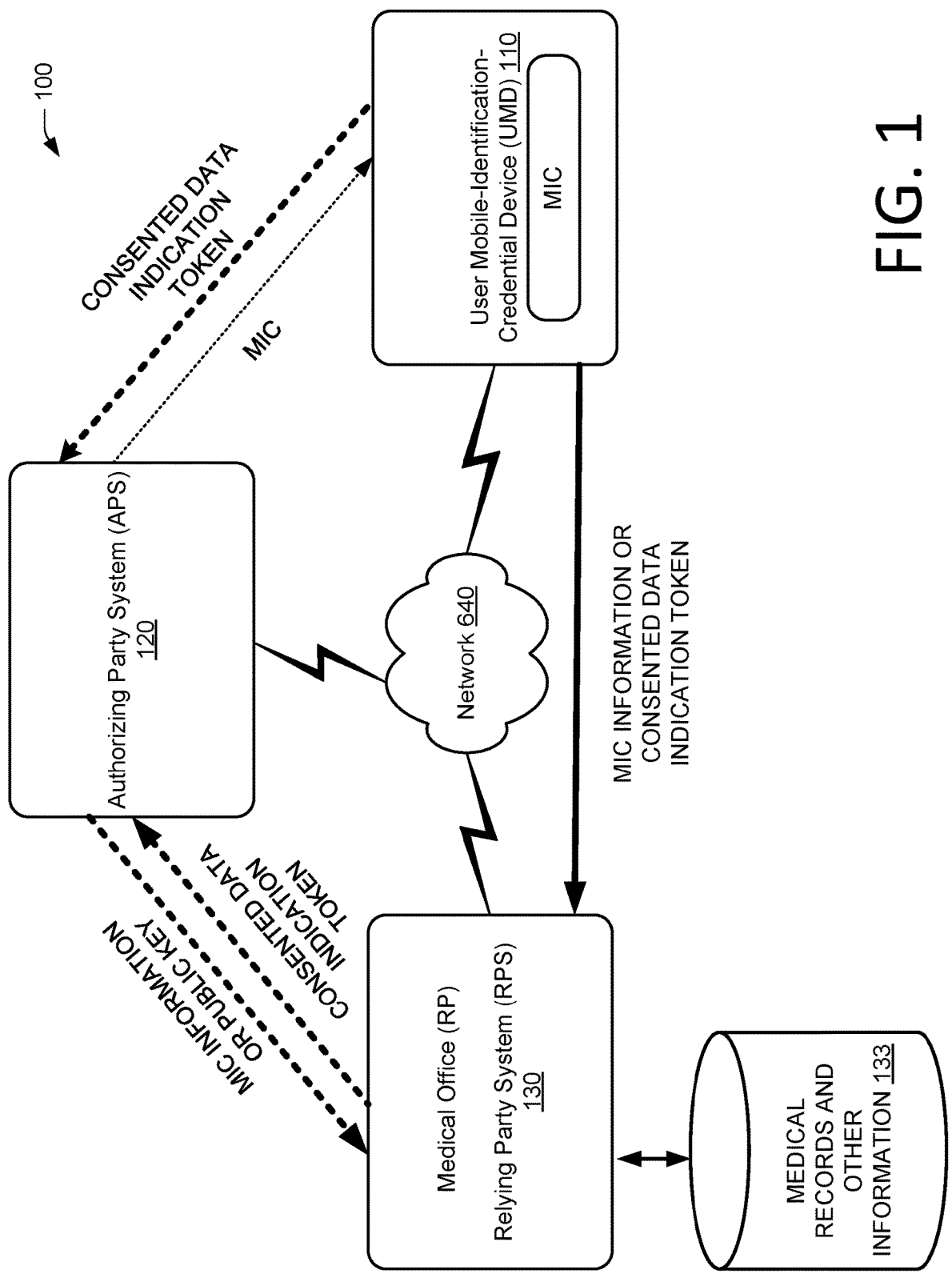
FIG. 1 shows an example of an overall system employing mobile identification credentials in processing a request to obtain a patient's medical record.

FIG. 1 shows an example of an overall system 100 employing mobile identification credentials to verify information of a patient requesting the patient's medical record. In an environment that supports its use, a Mobile Identification Credential (MIC) can enable a user to conveniently prove the user's identity. One embodiment of a MIC is a mobile driver's license (mDL) issued by an official agency such as a state Department of Motor Vehicles (DMV). Another embodiment of a MIC is a mobile passport. A mobile passport may, for example, be issued by the U.S. Department of State or a foreign ministry of another nation. The MIC can include various information, such as information relating to identity or privileges pertaining to the user.

The MIC itself may be portable and can be provisioned to devices. Below, the device to which the MIC is provisioned is referred to hereinafter as a User Mobile-Identification-Credential Device (UMD) 110. The term UMD pertains to any device to which a MIC can be provisioned including, without limitation, smart watches, smart fitness bands, smart objects, smart phones, e-readers, tablet computers, smart televisions and displays, smart cameras, laptop computers, desktop computers, servers, kiosks, chips, flash drives, and USB drives.

In an embodiment, the issuer of the MIC (the MIC Issuer) may provision and issue the valid, authentic MIC to the UMD. The MIC issuer may work with a MIC provider to facilitate the provisioning of the MIC to the UMD. The MIC Issuer also may work with a third party to provision the MIC to the UMD. In another embodiment, the user may provision the MIC from one device of the user to another device of the user (e.g., from the desktop computer to the smart fitness band).

A MIC may be validated by an Authorizing Party (AP). In one embodiment, the AP may be an official agency such as a state DMV. In another embodiment, the AP may be a third party empowered by an official agency to perform such verification operations. The AP employs an Authorizing Party System (APS) 120. The APS may provision the MIC to the UMD.

MIC Transactions

MIC transactions can be online or offline. Generally, the UMD 110 may interact or transact with other devices to share some or all of the content of the MIC. The device through which the UMD 110 shares the MIC user information is referred to as a Relying Party System (RPS) 130. The RPS is a system operated by or for a Relying Party (RP). The RPS may obtain MIC user information according to an online mode or an offline mode, based on the RPS's being able to trust the MIC user information and perform verification of the MIC user information, as enabled by the environment in which the MIC is used. In an online mode embodiment, the RPS 130 interacts with the APS 120 to verify the released MIC user information. In an offline mode, the RPS 130 may use a public key from the APS 120 to verify the released MIC user information. Generally, data transfers may be digitally signed, via electronic certificates, to verify authenticity of the data transferred. In addition to or instead of the use of digital signatures, data transfers may be encrypted via public-key cryptography to ensure integrity of the data transfers. Furthermore, data transfers can utilize tokenization to safeguard the online data transfers. Other embodiments rely on combinations of multiple such data protection procedures, as well as other data security best practices.

In some embodiments, secure local or remote connections may be established by using session keys, e.g., based on establishing session-specific encryption protocols. A session key is an encryption and decryption key that is randomly generated to ensure the security of a communications session between parties. A session key can be symmetric, used for encryption and decryption. A session key can be public or private. A session key can be ephemeral. As an example, usage of ephemeral public and private keys is described as follows. At initial engagement, a first device (Device 1) will pass its session public key to a second device (Device 2). Device 2 will use its private key and Device 1's public key to generate Device 2's public key. Device 2's public key is shared with Device 1. These ephemeral key pairs are used to encrypt and to decrypt messages sent between Device 1 and Device 2. A session begins when the two devices acknowledge each other and open a virtual connection, and ends when the two devices have obtained the information they request from one other and send "finished" messages, terminating the connection. Embodiments may make use of such session keys or other practices for establishing secure local or remote connections.

Online MIC Transactions

Online MIC transactions can involve trust and verification. An online MIC transaction may involve a UMD transferring MIC user information in response to a request from an RPS. The RPS verifies whether the received MIC user information is valid based on an online connection between the RPS and the APS. In an embodiment, the RPS may access an electronic certificate from the APS to verify the authenticity of the MIC user information received from the UMD. The UMD digitally signs the MIC user information using the electronic certificate from the APS. The UMD can retrieve the electronic certificate at the time of the transaction, either from the APS or from a certificate repository. In other embodiments, when something other than a public key is used to verify the MIC user information, the RPS may submit an electronic document or a digital file or the like to the APS in exchange for a key that may be referred to as an authentication key that is not public. The authentication key may be a public key that refreshes after a very short time, such that the RPS reaches out to the APS when it is time to verify the information and uses the public key with a short lifespan before it expires. In other embodiments, cryptography may be based on public-private key pairs.

The RPS or the UMD may perform a liveness check, e.g., by comparing collected biometric information to verified credentials. In an embodiment, an RPS may include a biometric sensor to capture biometric information of the user presenting at the RPS, such as a photograph, a video, a retina scan, a fingerprint, and the like. In another embodiment, the RPS may be configured to request a liveness check from the UMD. Due to the nature of the secure local connection as established through the handshake, the trustworthiness of information from the UMD responsive to the request is preserved. Accordingly, in an embodiment, the UMD may collect and transfer information that the RPS uses to perform the liveness check. For example, the UMD may collect a photograph, fingerprint, and accelerometer information that the RPS uses to determine whether the user's hand motions and/or walking gait are consistent with liveness check information known for the user. In another embodiment, the RPS determines that the UMD is deemed trustworthy for performing its own liveness check, and such UMD liveness determination performed by the UMD is accepted by the RPS. For example, the UMD may be a smartphone performing a facial recognition verification of the user, whose valid result the RPS accepts as verification that the proper user is legitimately in possession of the UMD and presenting the UMD at the RPS.

The interaction between the UMD and the RPS may be in-person, where a user is physically located at the RPS to present the UMD to the RPS. The interaction may be attended, where an attendant or other agent attending the RPS witnesses the transaction, to physically compare the appearance of the user, presenting the UMD at the RPS, against the MIC user information contained on the presented UMD. The interaction between the UMD and the RPS also may be remote, where a user is not physically located at or otherwise physically attending the interaction with RPS. For example, the user may be performing an online transaction using the UMD at home, which remotely transmits MIC user information over a remote connection from the UMD to the RPS located remote from the UMD, e.g., at an online web host.

Online MIC Transactions—Trust

The RPS needs to know, or trust, that the MIC user information obtained from the UMD is unchanged and matches official records. Part of this trustworthiness may be based on how the MIC was securely provisioned or placed onto the UMD, e.g., according to International Organization for Standardization (ISO) standards. Such secure provisioning enables the RPS to trust the MIC and its MIC user information, and also perform verification that such information matches official records pertaining to the person represented in the MIC user information. Trust also may be based on the reputation of the MIC issuer or the APS that provisioned the MIC onto the UMD. Trust further may be based on the trustworthiness of the connection between the RPS and the APS, e.g., based on a connection that is secured by encryption or other technological protections. In an embodiment, trust may be also based on the RPS reputation or other information about the RPS, such as Global Positioning System (GPS) coordinates, as detected by the UMD at the location of the transaction between the UMD and the RPS, matching known coordinates for that RPS.

Tokens can be used to establish trust, by exchanging tokens between the UMD, RPS, and APS. In an embodiment, a token or file may not actually contain requested MIC user information. Rather, the token or file may include a consented data indication to indicate which of the user's MIC user information is authorized for release. The APS can exchange the token or file for the MIC user information that is consented to be released by the APS to the RPS. When a user releases MIC user information from the UMD, the UMD passes an RPS token to the RPS and passes an APS token to the APS. The RPS may communicate via an online connection with the APS, which compares the APS token received from the UMD to the RPS token received from the RPS. Upon verifying a match, the APS provides a copy of the MIC user information to the RPS. Thus, the matching of tokens over an online connection enables the APS to trust the transaction and release the requested information, via an online connection, to the RPS. Tokens similarly enable the UMD or RPS to trust the transaction. In another embodiment, the UMD sends an RPS token to the RPS and sends an APS token to the APS; then, the APS releases the MIC user information only if both the RPS token and the APS token are received and only if within a given timeframe.

Online MIC Transactions—Verification

The RPS can verify that the MIC user information is trustworthy. The MIC, as provisioned onto the UMD including the MIC user information, may be electronically signed in an embodiment, to enable the RPS to verify that the MIC is provisioned to the proper UMD belonging to the proper user. Embodiments may use other or multiple data protection procedures, as well as other data security best practices to verify information, connections, transaction participants, or the like. In the online context, the RPS has an online connection to the APS. The online connection enables the RPS to request and receive information or verification directly from the APS. Accordingly, the RPS can perform online verification of MIC user information received locally from the UMD, by comparing the local information against information at the APS. The RPS also can perform a local verification of MIC user information received remotely from the APS, e.g., using data protection or verification procedures, or other data verification best practices.

Offline MIC Transactions

Trust and verification also play a role in offline, or disconnected, MIC transactions. The offline context refers to a condition when one or all parties in a transaction do not have an online connection to each other or to the Internet. For example, the RPS may be in an isolated location, or may be suffering from a communications failure, and therefore lack an online connection for communicating with the APS. Transactions may still proceed, by virtue of the ability of the RPS and UMD to establish a local connection with each other based on trust and verification. An offline MIC transaction may involve the RPS's verifying whether the received MIC user information is valid, without the RPS's having an online connection, e.g., without communicating to an external system such as the APS that can verify whether MIC user information received by the RPS is trustworthy. In an embodiment, the RPS verifies a cryptographic signature on the individual data elements of the MIC user information using, e.g., signer certificates. This ensures the data is genuine and unchanged, based on the RPS's performing a local verification based on cryptographic operations. In another embodiment, the RPS accesses a copy of an electronic certificate stored locally at the UMD, and periodically refreshes locally stored electronic certificates independently of a given transaction. In some instances, the RPS does not have to submit anything to the APS to obtain a public key for that APS, because the RPS keeps a locally stored copy of that APS key. In an embodiment, the RPS periodically checks with the APS to refresh the locally stored public keys. In some cases, there may be a public key distributor (PKD). The distributor would be an agent acting on behalf of several trusted entities. This agent would hold the most up-to-date public keys and distribute to trusted relying parties such as the RPS. Offline MIC transactions may be in-person, attended, or remote, as explained above in the context of online MIC transactions.

Offline MIC Transactions—Trust

Similar to the online context, the RPS can establish trustworthiness in a MIC and MIC user information for offline MIC transactions. As explained above, the RPS can verify that the MIC was securely provisioned or placed onto the UMD, and therefore trust the MIC and its MIC user information, based on cryptographic operations. Trust also may be based on reputations of systems that provisioned the MIC onto the UMD, and the trustworthiness of connections or the technological protections used between systems involved in transactions.

Offline MIC Transactions—Verification

The RPS can perform a local, offline verification that the MIC user information is trustworthy, without an online connection. For example, the RPS may perform local cryptographic operations to confirm electronic signatures of the MIC and MIC user information obtained from the UMD. In an embodiment, the RPS may use digital signatures or encryption to obtain, locally, verification of MIC user information. Such verification is possible when the RPS receives the MIC user information directly from the UMD instead of the APS, e.g., when the RPS is operating in an offline mode. Thus, the RPS does not contact the APS, but instead uses an offline stored public key of the APS to verify that the MIC user information is trustworthy as received from the UMD.

In the MIC environment presented in FIG. 1, a person presents a UMD 110 that includes MIC as part of an environment that supports MICs. The APS 120 electronically provisions the valid, authentic MIC onto the UMD 110, to ensure confidentiality, integrity, and authenticity of the MIC, or may have a third-party facilitate provisioning of the MIC to the UMD 110. The MIC may be associated with MIC information including biographics, biometrics, and other (such as privileges). The MIC may have a compartmentalized structure to enable the user to selectively control and release the information to relying parties. The provisioning of the MIC is done before the request for medical record and is thus indicated by a more lightly weighted arrow in FIG. 1.

Embodiments of the MIC environment may be compatible with multiple, different forms of identification (ID) and corresponding authorizing parties. The MIC may be capable of storing multiple different forms of ID simultaneously. For example, the MIC environment supports non-governmental forms of ID, including those from private companies, such as digital identification providers, third-party travel support providers, and the like. Embodiments may be compatible with forms of ID and their providers that are authorized by a governmental authority (or a non-governmental authority agreed upon by the relevant parties to the transaction) to provide and/or authorize credentials. For example, embodiments may be compatible with forms of employee IDs or other membership IDs such as real estate licenses, used to prove employment or other membership status (e.g., by including a verifiable employee ID number or other membership ID number).

Figure 3:
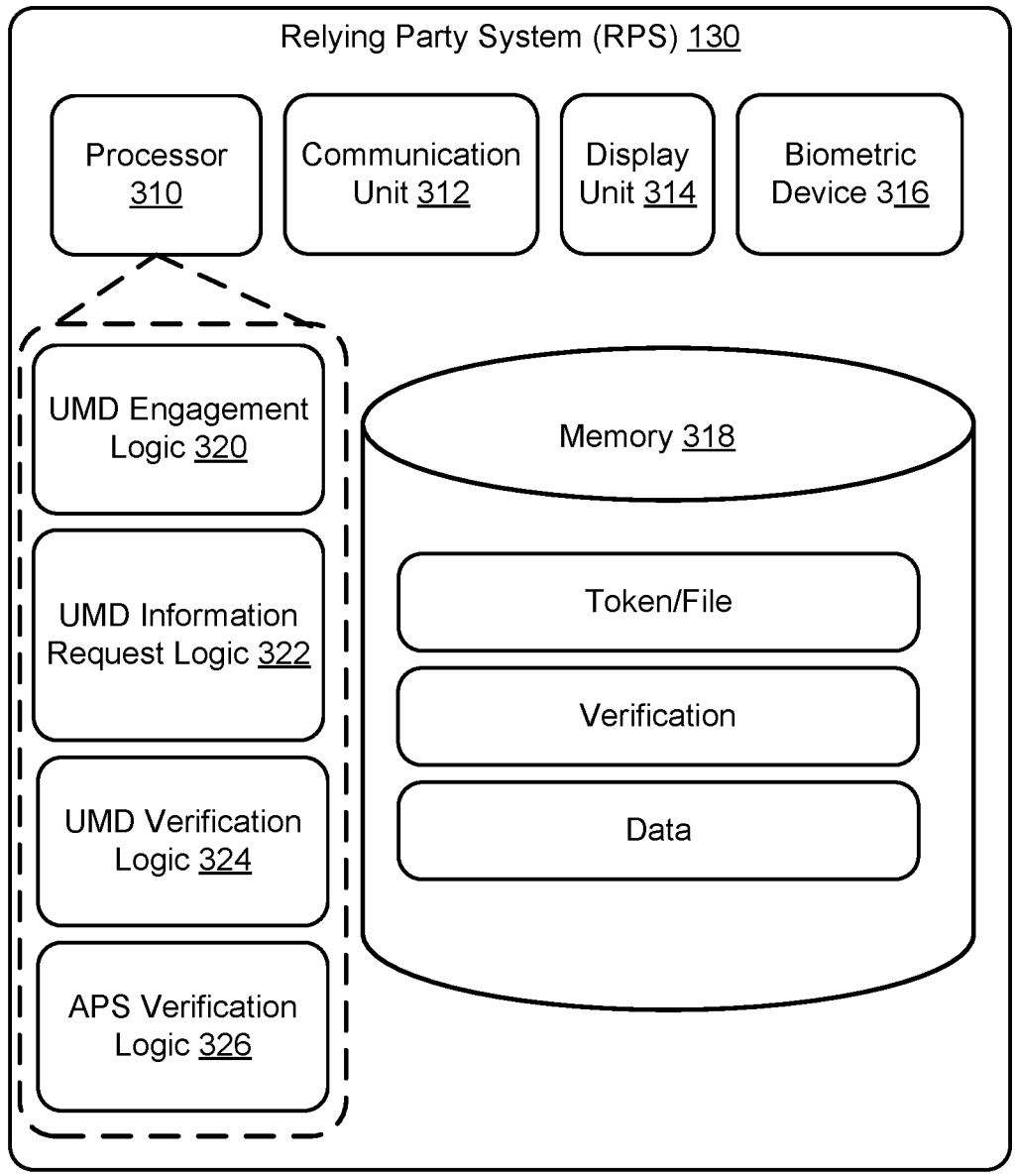
FIG. 3 illustrates a Relying Party System (RPS) according to an embodiment.
Figure 4:
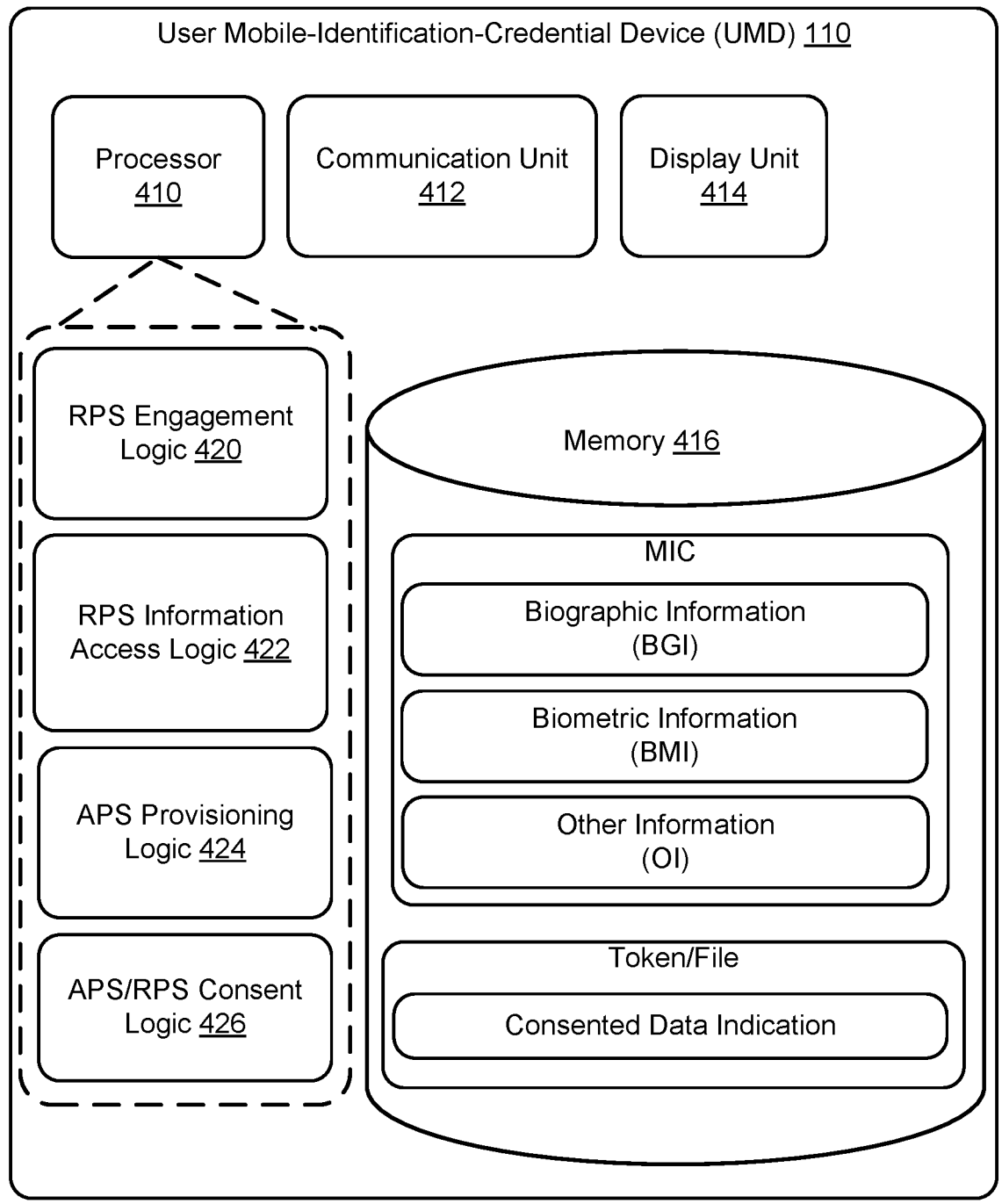
FIG. 4 illustrates a User Mobile-Identification-Credential Device (UMD) according to an embodiment.

As seen in FIG. 1, the UMD 110 interacts with another device to share some or all of the content of the MIC. The device that is to receive the MIC information is held by the medical office or some other medical or healthcare entity, which is a relying party that will rely on the information yielded via the MIC. The device of the relying party is the RPS 130. In some embodiments, the relying party has a database 133 of medical records and other information; such other information may include biographic information (e.g., age, gender, address, social security number, driver's license number, etc.) and/or biometric information (e.g., photograph, fingerprint, iris or retina scan, etc.). Such information can be used to conduct user verification independent of the use of the MIC information and/or can be updated for purposes of keeping the medical records of patients current. The network 640 facilitates communication between the UMD 110, APS 120, and RPS 130. Examples of the network 640 may include the Internet and a variety of different wired and wireless networks. Examples of the APS 120, RPS 130, and UMD 110 are illustrated in FIGS. 2-4.

Figure 2:
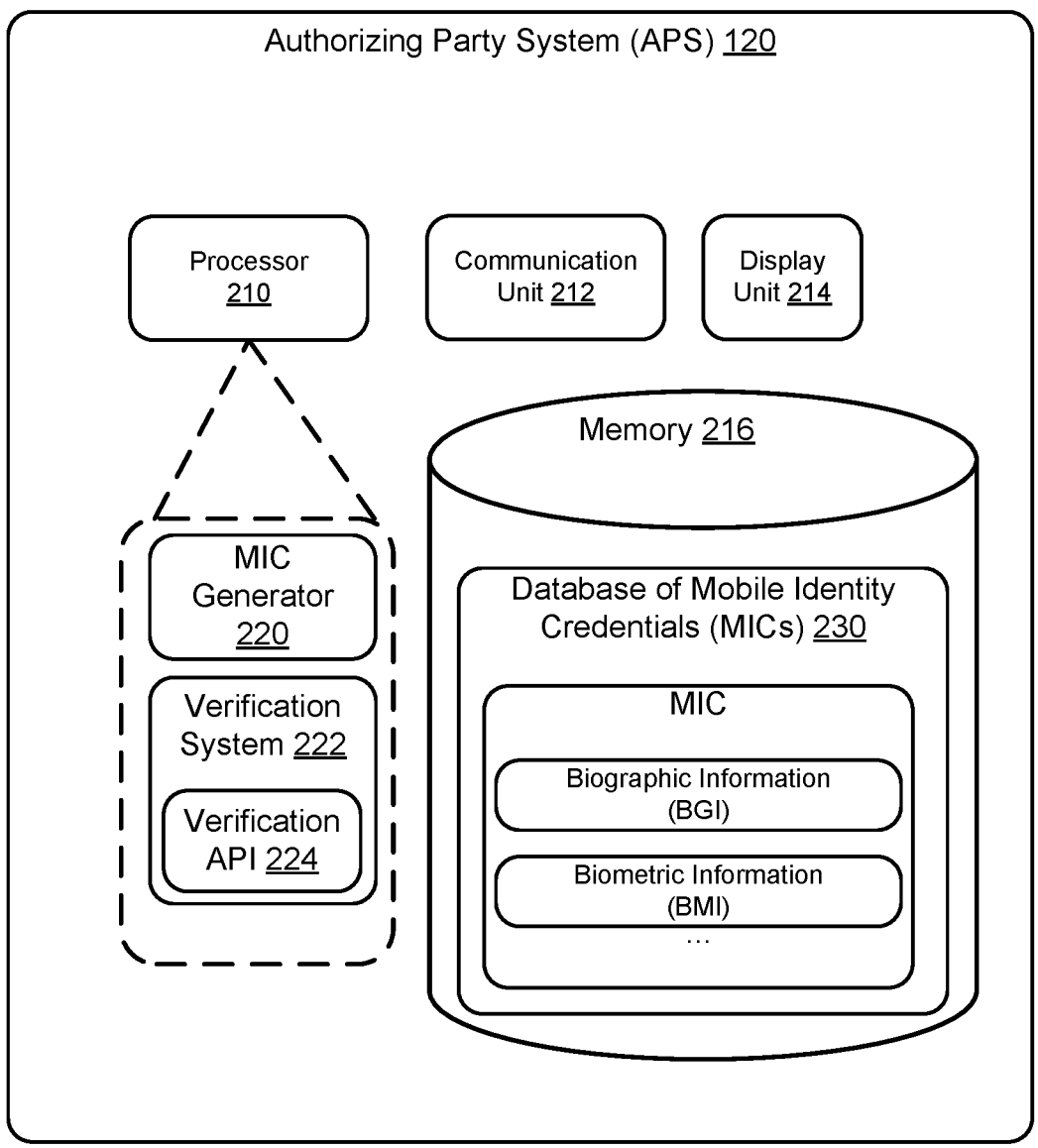
FIG. 2 illustrates an Authorizing Party System (APS) according to an embodiment.

FIG. 2 illustrates an Authorizing Party System (APS) 120 according to an embodiment. The APS 120 includes a processor 210, a communication unit 212, a display unit 214, and a memory 216. The processor may be associated with logic or modules to process information, including a MIC generator 220 and a verification system 222 with a verification Application Programming Interface (API) 224.

The MIC generator 220 enables the APS to generate a MIC for a given user. For example, the MIC generator receives unique information about the user, such as a social security number. The APS can reside in a local DMV office staffed with agents to verify physical documents in person, who traditionally verify that the social security number belongs to that user. The MIC generator creates a framework to build the MIC for the user and populates the MIC with corresponding biographic and biometric information, e.g., as available locally at the DMV office. In some embodiments, the MIC generator 220 may populate the MIC with other information corresponding to the user, such as driving privileges or special access. For example, the MIC can be issued or provisioned by the Federal Government, and may include special access, privileges, or MIC user information corresponding to positions at Federal Government agencies. In an example, the APS may be located at the DMV, and an agent of the DMV collects and manually verifies proof of identity that the user provides to the agent in person. In an embodiment, a kiosk at the DMV may perform a liveness check of the user and/or otherwise performs unattended verification of the proof of identity that the user provides to the kiosk.

In another embodiment, the MIC generator 220 facilitates verification of the user's identity attributes against official records available to the DMV and/or physically presented by the user. Facilitated verification can be attended by an agent in person, or unattended and self-performed by the user at a kiosk or other automated system. In an embodiment, such facilitated verification may involve the use of a system such as a kiosk or electronic device with audio or video playback and recording, visual scanning, or other telepresence capabilities, which the user accesses to interact remotely with an agent from the DMV or other APS that is to provision the MIC. Such a system can be located remote from the DMV or other APS facility, at which the agent is located, and can be separate from the UMD. In an embodiment, the system to interact with the agent may be the UMD that is to receive the MIC. Such system allows an agent at the DMV, through telepresence or other audio or visual interfaces of the system, to visually access, inspect, and verify information submitted as proof of identity (e.g., by scanning or photographing a birth certificate or the like). In another embodiment, such facilitated verification may involve the user's accessing a remote kiosk or smartphone app to virtually interact with an agent that facilitates the identity verification, or to interact with a self-guided verification user interface, such as a website or smartphone app.

Generated MICs may be stored in the memory of the APS and available for provisioning onto the UMD of the user. In an embodiment, a given APS provisions multiple different MICs onto the UMD, e.g., at an APS that provides a mDL and some other ID or proof. Examples include proof of residency and/or citizenship in cases where residency and/or citizenship confers some benefits.

Different types of MICs may be associated with corresponding different levels of assurance (such as multi-factor verification) needed to facilitate verification of the user's identity, whether in-person or remote, attended or unattended, or other aspects of the identity verification. Furthermore, in some embodiments, a given MIC environment may be associated with a corresponding trust framework, such as the transactions field (or the medical or healthcare field or the voting field) and a related set of rules pertinent to maintaining security of the transactions information (or the medical or healthcare information or the voting information). The level of assurance for a given MIC environment corresponds to the trust framework. Additionally, in an embodiment, communications with the MIC generator (and other aspects of the MIC environment including the APS, UMD, and RPS and their various modules or logic) may be facilitated and secured by cryptographic modules, e.g., as outlined in the National Institute of Standards and Technology (NIST) requirements and standards for cryptographic modules, the Federal Information Processing Standard (FIPS) publication 201 regarding Personal Identity Verification (PIV) requirements, and the like.

The verification system 222 of the APS 120 may be configured to interact with an RPS, such as when handling requests for user information received from an RPS. In the illustrated embodiment, the verification system uses a verification API to handle interactions in a standardized computing format.

The verification system 222 of the APS 120 also may be configured to interact with other systems, such as UMDs (to send or receive tokens), back ends, and the like. In an embodiment, the verification system may be configured to receive a token from the UMD, and a token from the RPS. The verification system then compares the tokens to determine whether the tokens match within an acceptable timeframe. In an embodiment, matching or otherwise verifying the two tokens indicates that the RPS is trustworthy regarding UMD consent and user information.

Generally, the APS verification system 222 verifies various aspects relating to MIC information. For example, the APS verification system may verify whether a request to release user MIC information is legitimate, and if so, authorize the release of such information. In an embodiment, the APS verification system authorizes release of MIC user information to the requesting RPS. In another embodiment, the APS verification system releases MIC user information to the UMD 110, e.g., when provisioning the MIC onto the UMD. In the illustrated example, the verification system uses a verification application programming interface (API) 224 to communicate with other systems requesting verification and/or MIC information, including RPSs and/or UMDs. In some embodiments, the verification system 222 of the APS 120 may be configured to communicate with other systems, such as other APSs including government entities, trusted certificate holders, open ID providers, back ends, and the like. The APS verification system enables such communications to be secure, ensuring the integrity of such communications.

The memory 216 may be associated with a database of MICs 230. A given MIC may include Biographic Information (BGI) and Biometric Information (BMI), which can be selectively requested and provided, e.g., as MIC user information, when the MIC is provisioned onto a UMD. The MIC also can include other information, such as privileges pertaining to the user.

The MIC generally may be structured to securely and discretely store various fields comprising the BGI, BMI, or other information. For example, the BGI may include first name, last name, date of birth, gender, address, identifier number, organ donor status, and the like. In an example, the BMI may include a digital photograph, a digital image representing a QR code containing the BGI, a digital fingerprint representation, a digital retina representation, and the like.

The structure of the MIC enables the other information to be added, such as when provisioning the MIC from the APS to a UMD, or after provisioning the MIC to the UMD, such as when the user enters information into the MIC via the UMD. For example, a user enters supplemental information into the MIC via the UMD, e.g., emergency contact information. Information on the MIC may be compartmentalized and separately accessible.

FIG. 3 illustrates a Relying Party System (RPS) 130 according to an embodiment. The RPS 130 includes a processor 310, a communication unit 312, a display unit 314, a biometric device 316, and a memory 318. The processor may be associated with logic or modules to process information, including UMD engagement logic 320, UMD information request logic 322, UMD verification logic 324, and APS verification logic 326. Embodiments of the RPS may include hardware (biometric device 316) to collect information to perform a liveness check of the user who is present at the location of the RPS, such as a camera, fingerprint reader, retina reader, and the like.

The biometric device 316 may include one or more biometric readers for obtaining biometric information from the user in person at the RPS 130, to be used to match authenticated biometric information in the MIC or otherwise stored in the APS 120 or the RPS 130. Examples include a fingerprint reader for fingerprint matching or recognition, a retina scanner for retina matching or recognition, a facial imaging device or camera for facial matching or recognition, and a voice recording device for voice matching or recognition.

The UMD engagement logic 320 may be configured to enable the RPS to establish a secure local connection with the user's UMD. For example, the UMD engagement logic establishes a key exchange protocol usable by the UMD, via radio frequency or visual communications. In an example, the UMD engagement logic encodes a public key in a QR code and displays the QR code to the UMD. Upon reading the QR code, the UMD responds to the RPS with a key exchange to secure a local connection between the RPS and the UMD. In some embodiments, the secure local connection utilizes protocols such as secure near-field, secure Bluetooth, secure Wi-Fi, or the like.

The RPS's UMD information request logic 322 may be configured to enable the RPS to structure a request for consent from the UMD and transmit that request to the UMD via a secure local connection. The request for consent includes a request for the types of user information which the relying party is requesting by way of the RPS. For example, the request for consent may include a request for the user's date of birth. The request for consent, in some embodiments, may include a dialog in which the user is prompted to answer specific questions, via a user interface, regarding whether the user releases the specific information fields, or a set of fields, to the RPS. In specific embodiments, this dialog is referred to as a release dialog.

The UMD verification logic 324 may be configured to enable the RPS to verify whether user information received from the UMD is valid, as set forth above in connection with online and offline MIC transactions.

The APS verification logic 326 may be configured to enable the RPS to verify whether user information received from the APS is valid. Similar to the online and offline approaches described above, the RPS can access an electronic certificate authorized by the APS, whether stored locally or remotely, to digitally verify information received from the APS that is digitally signed by the certificate used by the APS.

The memory 318 may be associated with a token/file, a verification, and data. The RPS makes use of tokens/files for trust and verification. The RPS receives the token/file from the UMD, and the RPS may be configured to pass the token/file to the APS. Thus, the RPS exchanges the token/file at the APS to receive user information. The verification represents a positive confirmation, via the use of electronic signatures or cryptography, that received information (whether from the APS or the UMD), is valid. The data represents the received user information.

FIG. 4 illustrates a UMD 110 according to an embodiment. The UMD includes a processor 410, a communication unit 412, a display unit 414, and a memory 416. The processor may be associated with logic or modules to process information, including RPS engagement logic 420, RPS information access logic 422, APS provisioning logic 424, and APS/RPS consent logic 426.

In an alternate embodiment, the UMD 110 may include removable memory, such as a Universal Serial Bus (USB) flash memory unit or micro Secure Digital (SD) flash memory card. In such embodiments, the memory of the UMD, which contains a provisioned MIC, may be separable from the UMD and/or combinable with a different UMD. In another embodiment, a memory itself serves as the UMD. In such embodiments, a user carries a portable memory UMD containing the user's MIC and/or user consent tokens/files. Such a portable memory UMD, in embodiments, may be a portable USB flash drive. To conduct a transaction or otherwise provide identification, the user inserts the portable memory into an RPS 130, which interprets the insertion as proximal consent to read the MIC user information (whether directly from the portable memory to the RPS in an offline mode, or indirectly by retrieving a user consent token from the portable memory and forwarding that token to an APS 120 from which the RPS receives MIC user information). In yet another embodiment, the UMD comprises a code, such as an electrically-readable code via magnet, RFID, and the like, or an optically readable code such as barcode, QR code, and the like. In such embodiments, the user conducts a transaction or otherwise provides identification by presenting the code to an RPS including a reader compatible with the code's format. In an embodiment, the RPS may include a keyboard that the user uses to manually type the code. In another embodiment, the RPS may include a card reader to read the code contained in or on a card-format UMD, whether electronically, magnetically, or optically encoded on the card. The RPS reader can verify such identities by using those forms of identity to retrieve biometric information from the APS and performing a comparison with the user to verify that the MIC belongs to that user. In yet another embodiment, the UMD may be a personal identity verification (PIV) card.

The RPS engagement logic 420 may be configured to enable the UMD to establish the secure local connection with the RPS, as set forth above with respect to the description of FIG. 3.

The RPS information access logic 422 may be configured to enable the UMD to allow the RPS to access the MIC user information associated with the MIC (whether stored at the UMD for offline mode access or stored at the APS for online mode access). In the context of allowing access to MIC user information stored on the UMD, passive access involves the UMD enabling the RPS to read data from the UMD. Active access involves the UMD transmitting data to the RPS. Allowing access furthermore may include the UMD authorizing release of MIC user information from the APS to the RPS, which similarly involves passive or active access between the RPS and the APS. The RPS information access logic 422 may be responsive to the UMD information request logic, as set forth above with respect to the description of FIG. 3.

The APS provisioning logic 424 may be configured to enable the UMD to receive a MIC from the APS and store the received MIC securely on the UMD. The APS provisioning logic may be responsive to the MIC generator as set forth above and as described in connection with FIG. 2. In an embodiment, the APS provisioning logic communicates with the APS to indicate readiness for provisioning the MIC from the APS onto the UMD. In some embodiments, the APS provisioning logic may be configured to provision multiple MICs onto the UMD. For example, the APS provisioning logic provisions a first MIC corresponding to a mobile Driver's License (mDL), and a second MIC corresponding to some other ID or proof such as, e.g., proof of residency and/or citizenship in cases where residency and/or citizenship confers some benefits. The UMD stores the MIC in the memory as illustrated, including the various information of the MIC such as the BGI, BMI, and OI.

The APS/RPS consent logic 426 may be configured to enable the UMD to receive requests for the consent and release of MIC information. The APS/RPS consent logic may be configured to generate, responsive to received requests, corresponding compartmentalized and/or discrete prompts for the user's consent to selectively indicate approval to release such MIC information. In an example, the APS/RPS consent logic may be configured to interact with the UMD information request logic, as set forth above and described in connection with FIG. 3. In an embodiment, the APS/RPS consent logic receives the user's selective consent and sends the consent to the APS whereby the APS acts in accordance with the consent. In another embodiment, the APS/RPS consent logic receives the user's selective consent and directs the UMD to selectively release the MIC user information in accordance with the consent.

The memory 416 may be associated with at least one MIC and a Token/File. The MIC may include MIC user information such as Biographic Information (BGI), Biometric Information (BMI), and Other Information (01) such as privileges. The Token/File may include a consented data indication. In an offline embodiment, the APS/RPS consent logic obtains consent and transmits the requested BGI, BMI, and/or OI (e.g., using a secure communication link and a verification protocol to digitally sign the requested information) from the UMD to the RPS. In an online embodiment, the APS/RPS consent logic obtains consent and transmits, to the APS, the token/file (as stored in the memory) which contains a consented data indication. The token/file does not actually contain the requested MIC information. Rather, the token/file may include the consented data indication which indicates which of the user's MIC information is authorized for release by the APS. Such consented data indication may be used by the RPS. The RPS passes the consented data indication to the APS, which exchanges the token/file for the MIC user information that is consented to be released. The APS then releases to the RPS (e.g., allows access by the RPS) the consented MIC user information.

As used herein, a UMD is not required to be mobile. It is meant to encompass stationary devices such as desktop computers and portable devices such as laptop and notebook computers as well as mobile telephones. In a specific embodiment, the requested MIC may be transmitted from the APS to a stationary intermediary device, which serves as the UMD that subsequently transmits the MIC to a user mobile telephone. This is a typical example of a request made from a remote location such as a person's home using the person's computer as the UMD.

In addition, while the above describes that the user uses the UMD to interact with the medical office system to request a medical record by verifying the identity of the user, other ways of verifying the identity of the user are possible. In one example, the user presents to the RPS the MIC in the form of a computer-readable storage medium such as a USB dongle instead of a UMD. For example, the storage medium may be a removable memory from the UMD. In such a scenario, the RPS may be configured to read the MIC from the user's storage medium and, optionally, receives input from the user via a user interface consenting to access part or all of the MIC information and/or decrypting the stored data if necessary. At the end of the user verification process, when all verifications are done, the RPS provides the requested physical medical record to the user in person and/or transfers an electronic medical record to the user's storage medium. Proper procedures are followed to ensure compliance with Health Insurance Portability and Accountability Act of 1996 (HIPAA) in handling electronic protected health information.

In yet another embodiment, instead of using a UMD or a computer-readable storage medium, the user may present to the RPS, in person or remotely, an electronic key or digital code, which the RPS can use to access the user's MIC stored in a third-party storage medium, such as a cloud storage medium. At the end of the user verification process, when all verifications are done, the RPS provides the requested physical medical record to the user in person and/or transfers an electronic medical record to the patient via e-mail or the like.

Process Embodiments

To verify the identity of the user, the RPS 130 requests user ID information of the user, which may include some or all of the content of the MIC. The user has the option of consenting to release selectively some or all of the requested information. It may include age and residency information (e.g., utility bills to establish residency), and may further include citizenship information (e.g., passport or birth certificate to establish citizenship), etc. If the requested user information provided appears suspicious, additional information may be required. For instance, the UMD may provide the location history and travel pattern that can be used as evidence to support the user's residency claim (consistent evidence) or refute the user's residency claim (inconsistent evidence).

Figure 5:
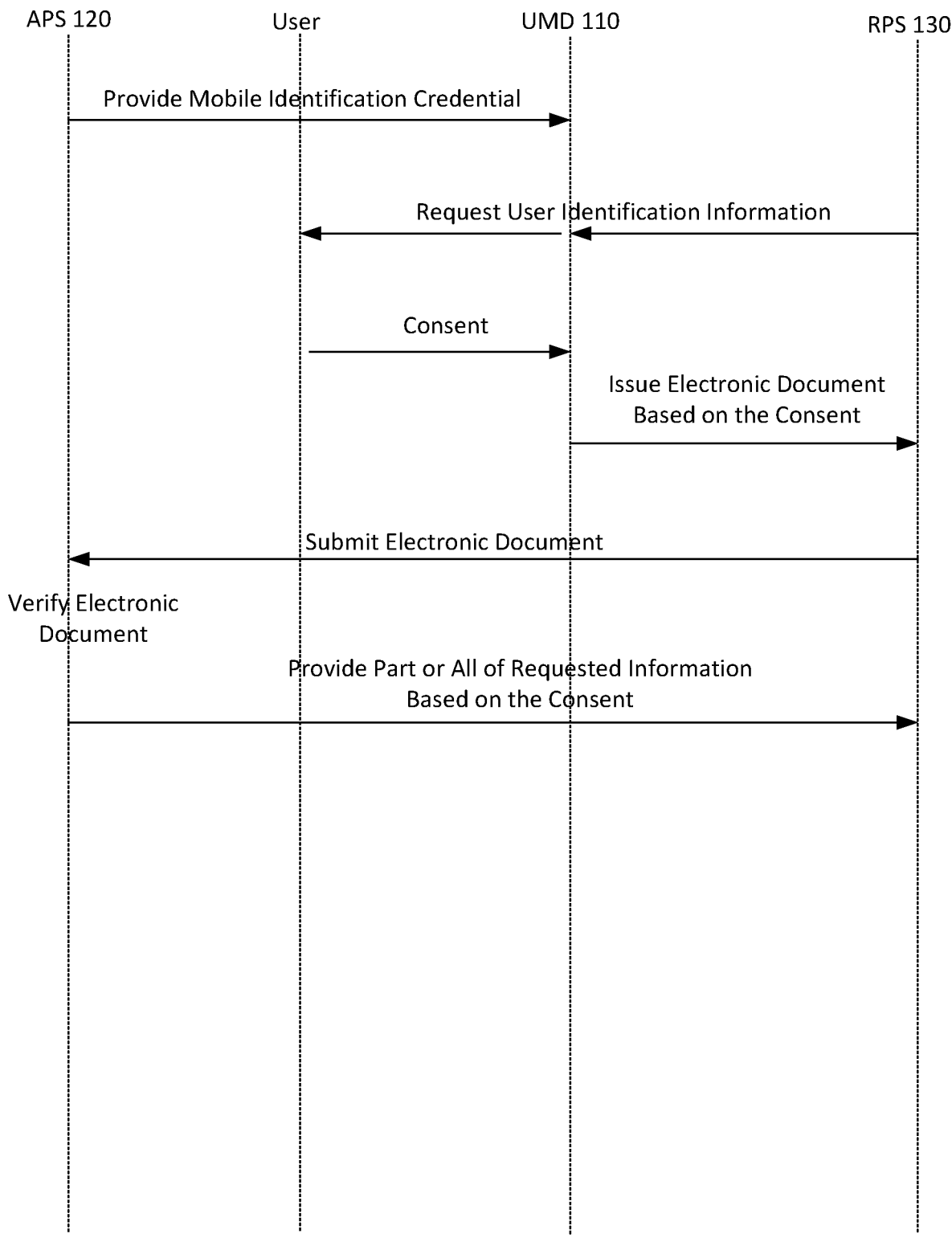
FIG. 5 illustrates verifying information of a patient requesting medical record using mobile identification credential (MIC) according to an embodiment.

In an embodiment illustrated in FIG. 5, the user of the UMD 110 requests his or her medical record from the RPS 130. In response to a request for user identification (ID) information from the RPS 130, the UMD 110, having received the MIC from the APS 120, may issue an electronic document or a digital file such as a digital certificate or a key with consented data indication, based on the user's consent, to the RPS 130. The relying party may be the medical office or some other medical entity that has the patient's medical record. The RPS 130 may submit the electronic document to the APS 120. Upon verification of the electronic document, the APS may provide some or all of the requested information which is associated with the MIC to the RPS 130, as determined by the scope of the consent. For instance, if establishing user identity is the only concern, the user may choose to release only information sufficient to establish identity and none of the other information that is not relevant (such as age, race, gender, national origin, passport, birth certificate, etc.). When the identity of the user is verified to the satisfaction of the relying party, the RPS 130 will provide the requested medical record to the UMD 110 or its user. A physical medical record can be provided to the user in person or mailed to the user. An electronic medical record can be downloaded or otherwise transferred to the UMD 110. A similar process is employed when the request is made by the user from a remote location except that the medical record may be issued only electronically to the UMD 110. Proper procedures are followed to ensure compliance with HIPAA in handling electronic protected health information. When the received electronic document is not verified by the APS, the APS 120 sends the UMD 110 a notification to resubmit the request for user ID information.

Figure 6:
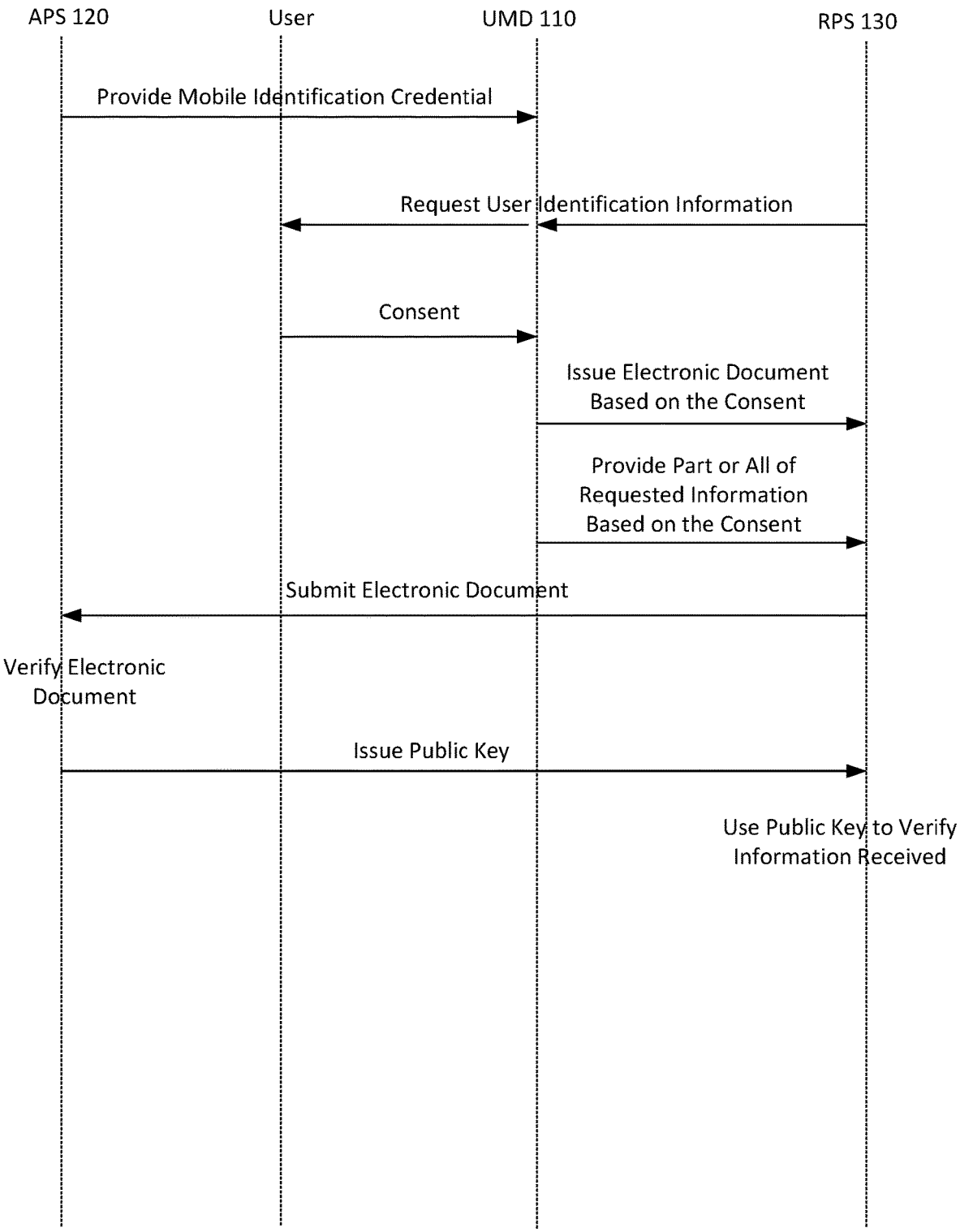
FIG. 6 illustrates verifying information of a patient requesting medical record using MIC according to another embodiment.

In another embodiment illustrated in FIG. 6, the UMD 110, having received the MIC from the APS 120, receives a request for user ID information from the RPS 130. In response, the UMD 110 may issue an electronic document or a digital file, based on the user's consent, to the RPS 130. In addition, the UMD 110 may provide to the RPS 130 part or all of the requested information, which is associated with the MIC, based on the consent. The RPS 130 may submit the electronic document to the APS 120. Upon verification of the electronic document, the APS 120 may issue a public key to the RPS 130. The RPS 130 may use the public key to verify the information received from the UMD 110. In specific embodiments, the information was encrypted or digitally signed using a private key and the public key is used to decrypt the encrypted information or read the digitally signed information. When the identity of the user is verified, the RPS 130 can provide the medical record to the patient or the UMD 110.

In some instances, the RPS 130 does not have to submit anything to the APS 120 to obtain the public key. In general, the only time the RPS 130 will have to go to the APS 120 is to refresh the public keys. In some cases, there may be a public key distributor (PKD). The distributor would be an agent acting on behalf of several trusted entities. This agent would hold the most up-to-date public keys and distribute to trusted relying parties.

The use of a public key to authenticate a digital signature or the like is merely an example. In other embodiments, the APS 120 may issue another electronic document or digital file or the like (e.g., referred to as an "authentication key")

which the RPS 130 can use to verify that the information received from the UMD 110 can be trusted to establish the identity of the user (i.e., to verify the authenticity of the information received). In one example, the authentication key may be a public key that refreshes after a very short time, thereby prompting the RPS 130 to reach out to the APS 120 when it is time to verify the information and use the public key with a short lifespan before it expires.

When the received electronic document is not verified by the APS, the APS 120 may send the RPS 130 a notification to resubmit the request for identification information of the patient/user. When the identity of the user is verified to the satisfaction of the relying party, the RPS 130 can release the requested medical record to the patient which can involve physical transfer, shipping, or digital transfer to the UMD 110.

Figure 7:
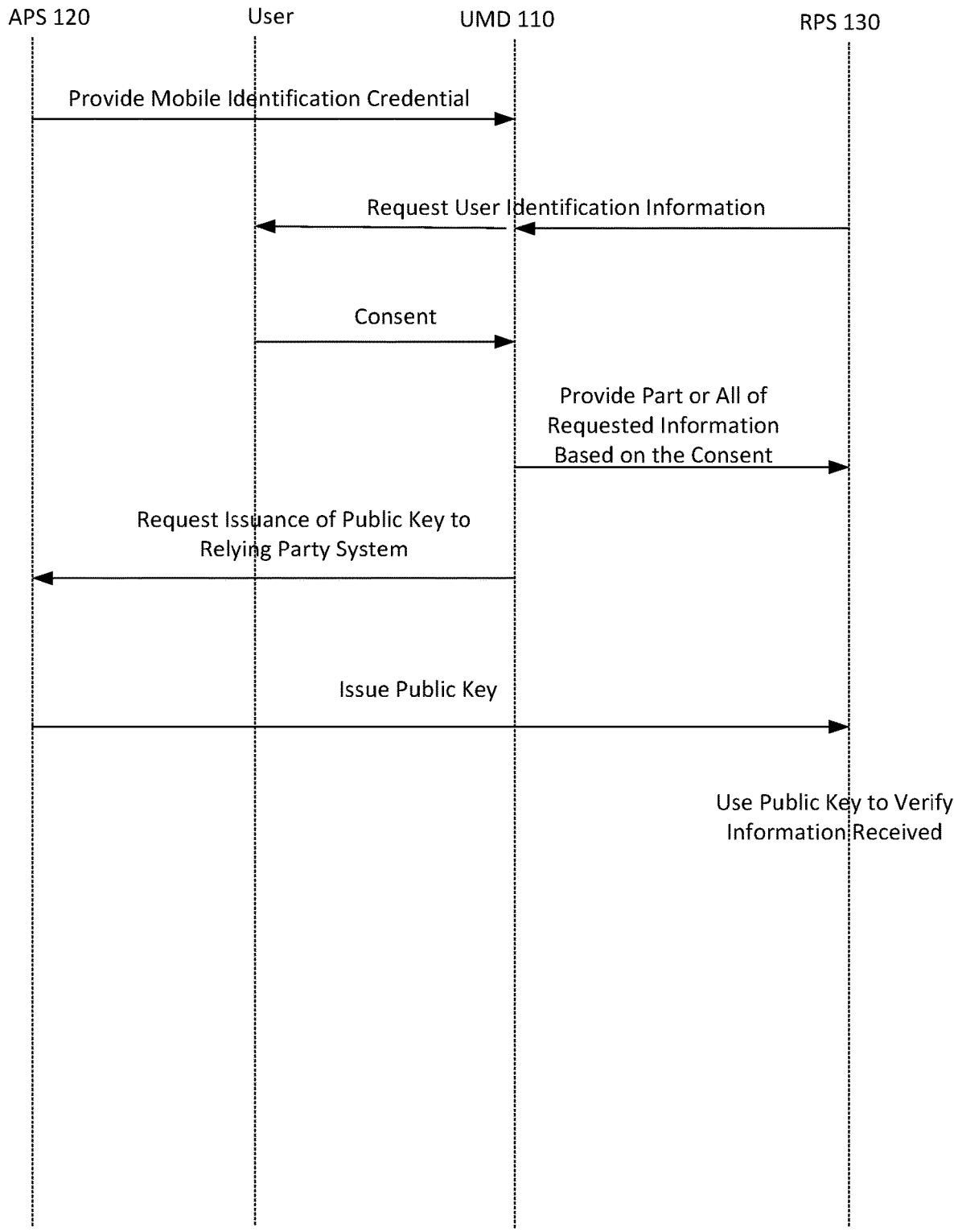
FIG. 7 illustrates verifying information of a patient requesting medical record using MIC according to another embodiment.

In another embodiment illustrated in FIG. 7, the UMD 110, having received the MIC from the APS 120, receives a request for user ID information from the RPS 130 and provides part or all of the requested information associated with the MIC to the RPS 130 based on the user's consent. The UMD 110 may request that the APS 120 issue a public key to the RPS 130. The APS 120 may issue the public key to the RPS 130, which uses the public key to verify the information received from the UMD 110. Again, the public key is merely an example. It can be replaced with another electronic document or digital file or the like (e.g., "authentication key") which the RPS 130 can use to verify that the information received from the UMD 110 can be trusted to establish the identity of the user. When the identity of the user is verified to the satisfaction of the relying party, the RPS 130 can release the requested medical record to the user which can involve physical transfer, shipping, or digital transfer to the UMD 110.

Figure 8:
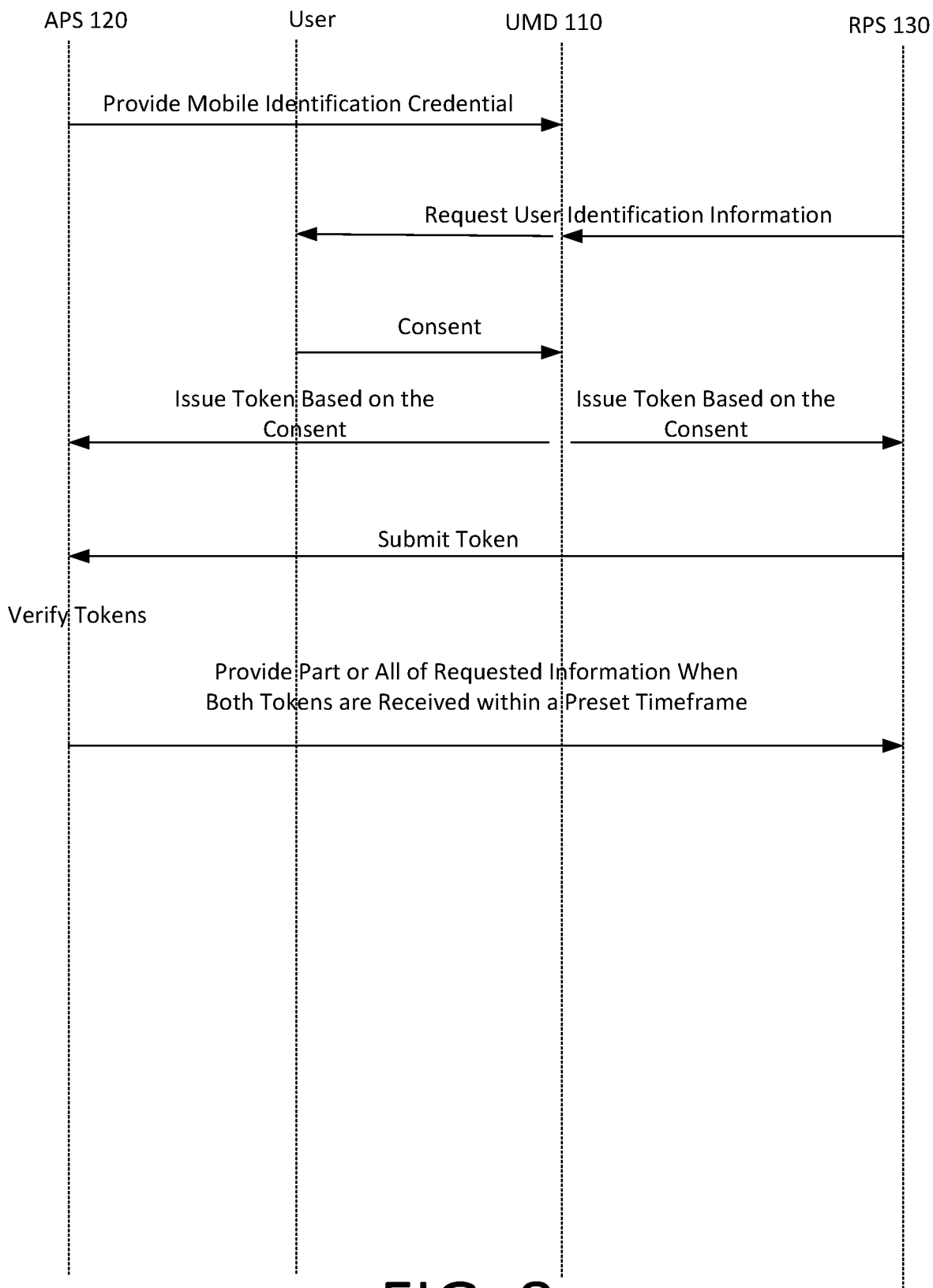
FIG. 8 illustrates verifying information of a patient requesting medical record using MIC according to another embodiment.

In another embodiment illustrated in FIG. 8, the UMD 110, having received the MIC from the APS 120, receives a request for user ID information from the RPS 130. In response, the UMD 110 may issue, based on the user's consent, a token to the RPS 130 and another token to the APS 120. The RPS 130 may submit the received token to the APS 120. When both tokens are received within a preset timeframe (e.g., within 30 minutes, within 10 minutes, within 3 minutes, within 1 minute, within 30 seconds, etc.) and are matched or otherwise verified by the APS, the APS 120 may provide part or all of the requested information associated with the MIC to the RPS 130. When the tokens are not received by the APS within the preset timeframe or are not verified by the APS, the APS 120 may send a notification to the RPS 130 to resubmit the request for ID information of the user. When the identity of the patient is verified to the satisfaction of the relying party, the RPS 130 can release the requested medical record to the patient which can involve physical transfer, shipping, or digital transfer to the UMD 110.

In an embodiment, when the user requests the item from a remote location or at an unattended kiosk, the system may incorporate a liveness check as described above. The liveness check ensures that the person making the request for the medical record via the UMD 110 is the proper user of the UMD 110 instead of someone else who has taken control of or gain access to the UMD 110 or instead of a bot.

Figure 9:
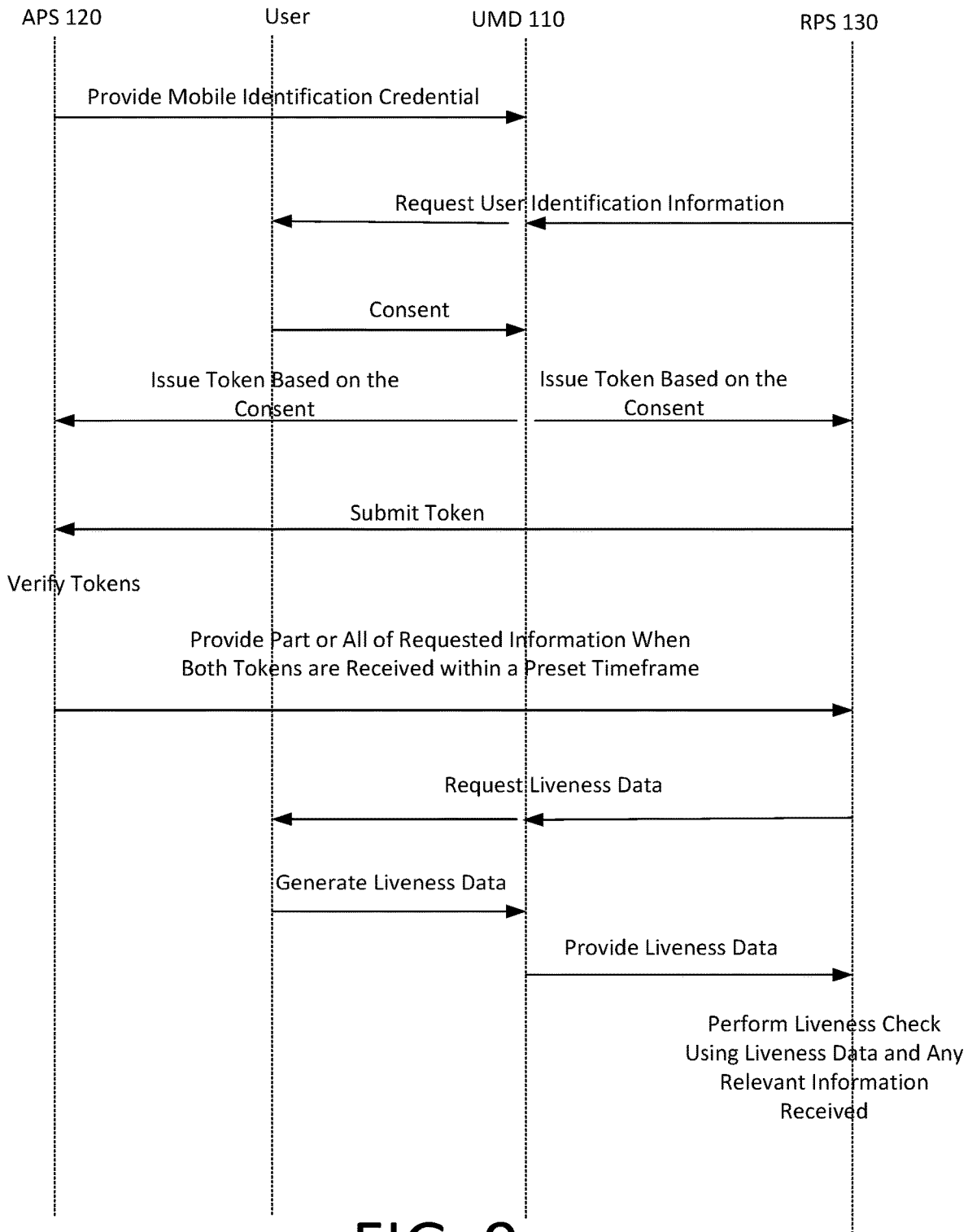
FIG. 9 illustrates performing a liveness check of a patient requesting medical record according to an embodiment.

In another embodiment illustrated in FIG. 9, which builds upon FIG. 8, the RPS 130 requests liveness data from the UMD 110. The user may generate the liveness data using the UMD 110, which provides the liveness data to the RPS 130. Examples of the liveness data include a live facial image, a live video, a live iris or retina scan, and a live fingerprint scan of the user taken using the UMD 110. While a liveness check that involves biometrics is generally more reliable, it does not require biometrics and can involve taking certain live actions that can be detected and verified. The RPS 130 performs the liveness check using the liveness data and any relevant information received (e.g., comparing the live image or video with a photograph of the user contained in the MIC). While the embodiment illustrated in FIG. 9 shows that the liveness check is performed after the identity verification process, the order can be reversed in other embodiments.

Figure 10:
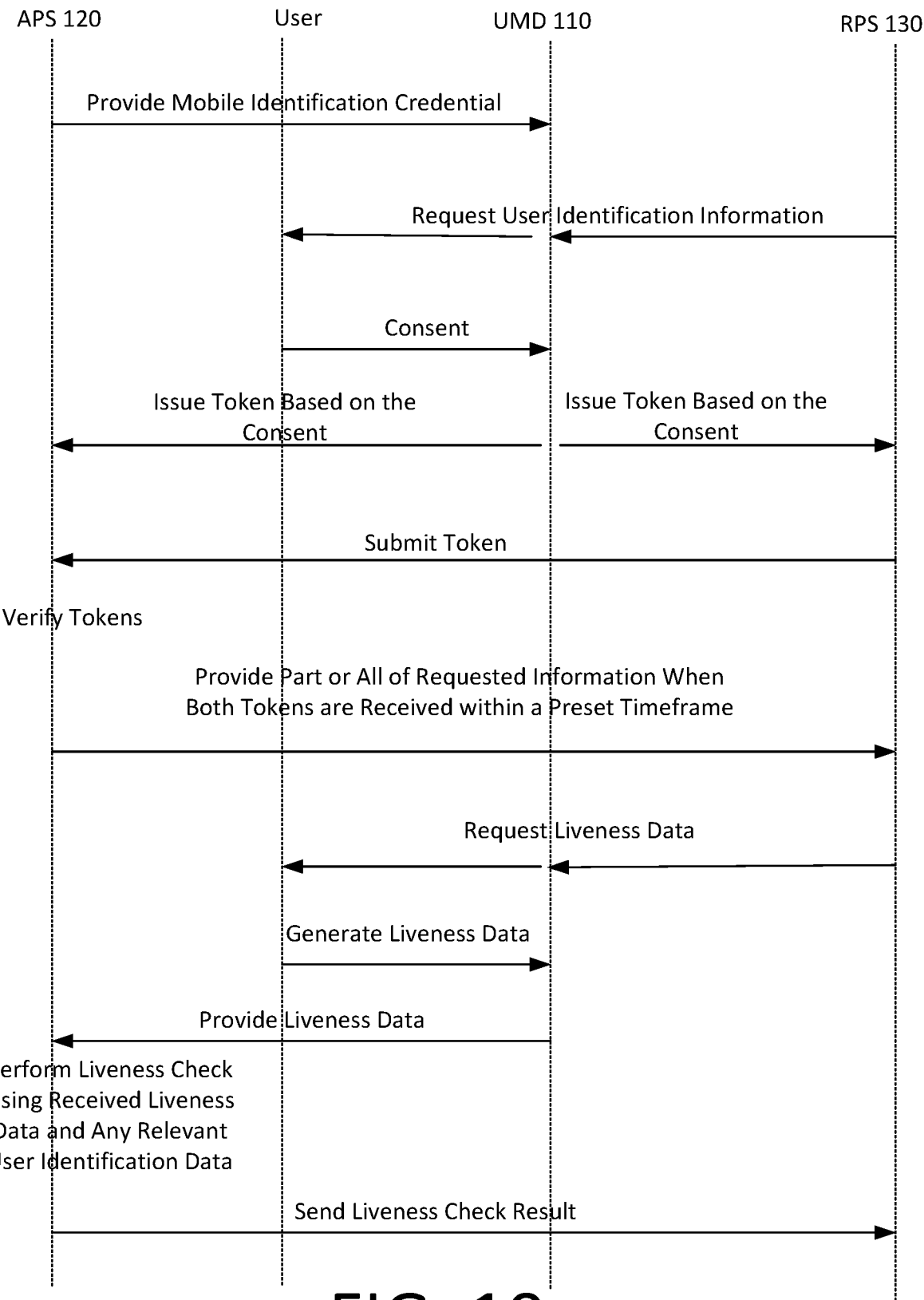
FIG. 10 illustrates performing a liveness check of a patient requesting medical record according to another embodiment.

In another embodiment illustrated in FIG. 10, which builds upon FIG. 8, the RPS 130 requests liveness data from the UMD 110. The user may generate the liveness data using the UMD 110, but instead of providing the liveness data to the RPS 130 as in FIG. 9, the UMD 110 provides the liveness data to the APS 120. The APS 120 may perform the liveness check using the received liveness data and any relevant user information such as stored user ID data (e.g., contained in the MIC), and sends the liveness check result to the RPS 130.

Other embodiments of identity verification are possible. For instance, different features of the processes of FIGS. 5-10 can be combined to create new embodiments.

The embodiments in FIGS. 5-10 show devices that connect to the APS 120, e.g., via the Internet, during the request for medical record. The RPS 130 can obtain, directly from the APS 120, the MIC information (FIGS. 5 and 8) or a public key or some other electronic document or digital file to verify the authenticity of the MIC information that the RPS 130 has received (FIGS. 6 and 7). Signer Certificates or the like from a Trust List can be used to validate the Base URLs of the APS 120.

When there is no connection with the APS during the request for medical record, local transmission links between the UMD 110 and the RPS 130 can be made through directed action by the UMD 110 such as a tap or showing a QR code to the RPS 130. The connection may then be secured by standardized key exchange and encryption of the transport of data. The RPS 130 can verify that the data received from the UMD 110 is valid and unchanged using Signer Certificates from a Trust List, or the public key of the APS which is available, or the like. The process ensures that the MIC information received by the RPS 130 from the UMD 110 was not cloned from another, different UMD.

Figure 11:
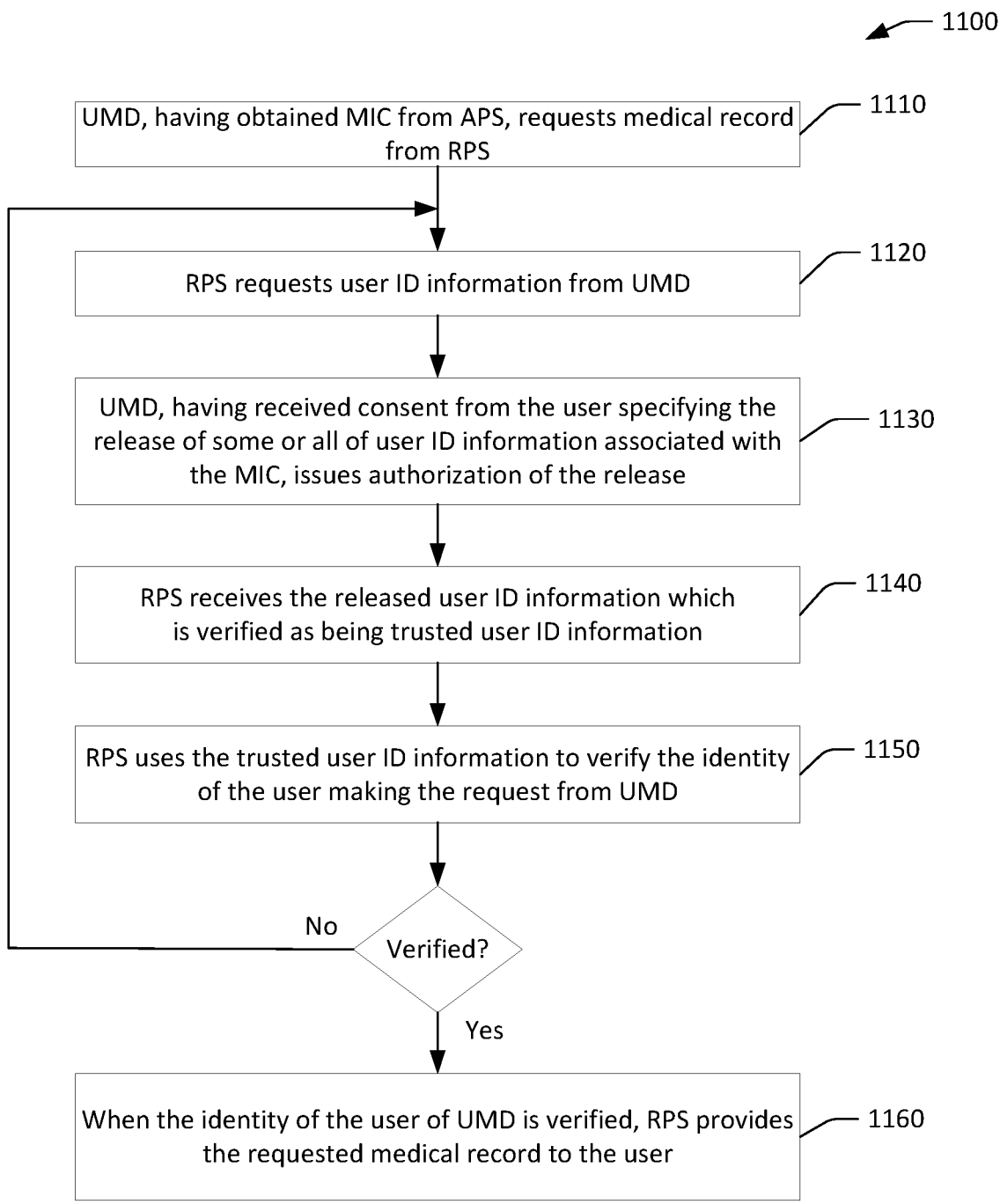
FIG. 11 is a flow diagram illustrating an embodiment of a process for a patient to request the patient's medical record.

FIG. 11 is a flow diagram 1100 illustrating an embodiment of a process for a patient to request the patient's medical record. In step 1110, the UMD (e.g., patient's device), having obtained the MIC from the APS (e.g., DMV system), requests medical record of the patient from the RPS (e.g., medical office) using a secure connection, for instance, via a secure network. The UMD in this example is presented at the medical office or some other device (stationary or mobile) from a remote location. One way to establish a secure connection is by using session keys, as described above.

In step 1120, the RPS requests patient/user ID information from the UMD in response to the request for medical record. The user may be notified of the request via a display or some other user interface on the UMD, and may give consent via a user interface of the UMD to release some or all of the requested user ID information associated with the MIC. In step 1130, the UMD issues authorization of the release, based on the user's consent, to the RPS or the APS in different embodiments. In some embodiments, the authorization may take the form of a token, an electronic document, a digital file, or the like issued from the UMD to the RPS and then submitted by the RPS to the APS seeking verification of the token, electronic document, digital file, or the like via the secure network. In some other embodiments, the authorization may be a direct request from the RPS to the APS or a token sent from the UMD to the APS to be matched with another token sent from the RPS to the APS.

In step 1140, the RPS receives the released user ID information which is verified as being trusted user ID information. In different embodiments, the APS may receive the authorization from the UMD (e.g., direct request in FIG. 7 or token in FIG. 8) or may examine the authorization from the RPS (e.g., electronic documents in FIGS. 5 and 6 or token in FIG. 8) for verification or nonverification. When the authorization is verified, it establishes that the user ID information received by the RPS is valid and can be trusted. In some embodiments, the RPS may receive and use a public key or some other electronic document or digital file to verify that the user ID information received from the UMD is trustworthy.

Next, the RPS uses the trusted user ID information, which may be received from the UMD or the APS, to verify the identity of the user who requests the medical record using the UMD in step 1150. In some cases, the verification involves matching the user's name. In other cases, more may be required to satisfy the RPS. For instance, the verification may involve matching other biographic and/or biometric information and/or additional information. What is required may depend on the nature of the medical record transaction. For an in-person request for medical record, any biographic or biometric information can be obtained live from the person at the RPS using biometric devices or readers (e.g., fingerprint matching or recognition by a fingerprint reader, iris or retina matching or recognition by iris or retina scanner, facial matching or recognition by a facial imaging device, voice matching or recognition by a voice recording device, etc.). For online request for medical record, such information can be obtained from a trusted source and/or a liveness check can be required to obtain the biometric information. If the identity of the user is not verified, the RPS may request resubmission of the user ID information from the UMD.

In step 1160, when the identity of the user from the UMD is verified to the satisfaction of the RPS, the RPS provides the requested medical record to the UMD. For an in-person request, a physical medical record is given to the user. Alternatively, it may be transmitted or downloaded to the UMD.

Figure 12:
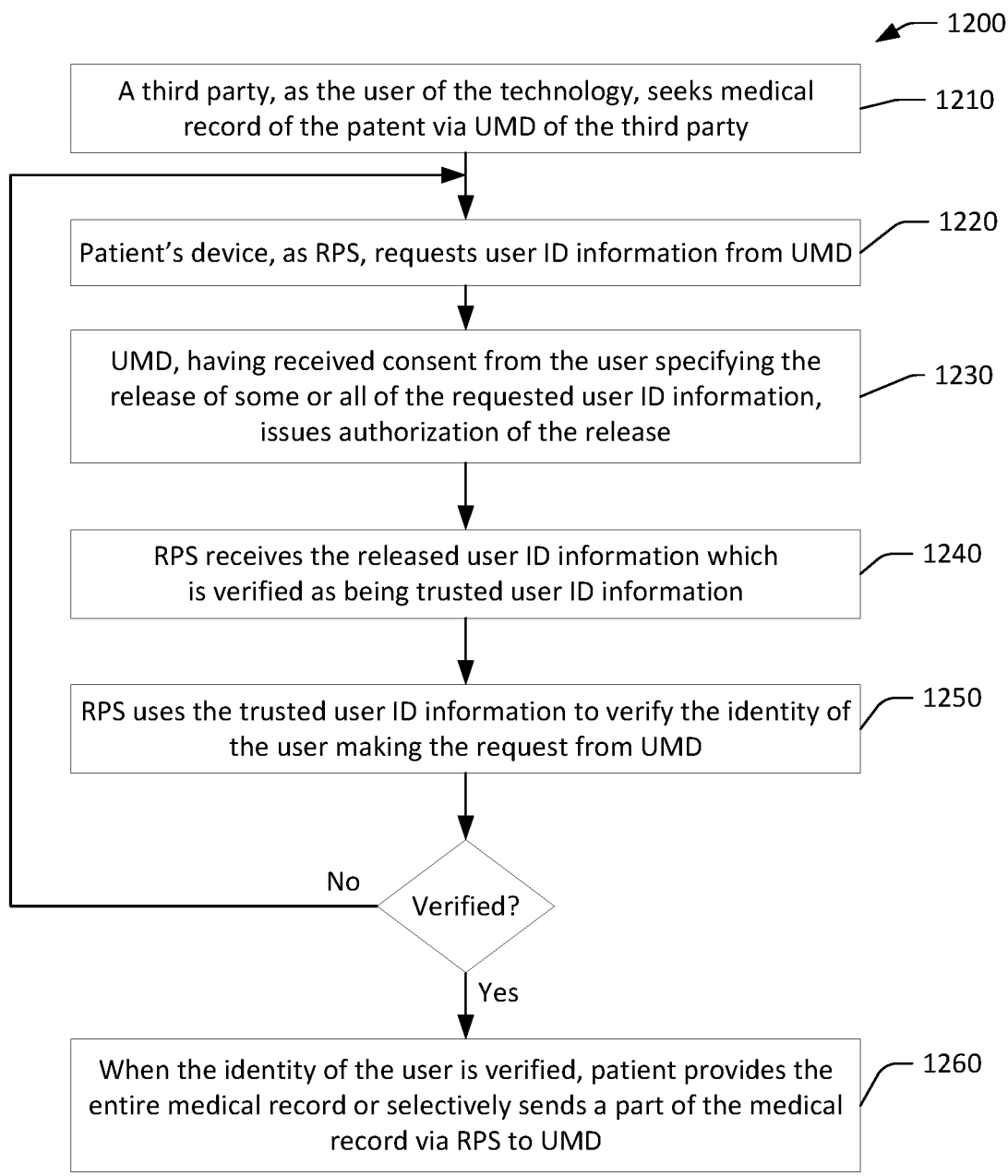
FIG. 12 is a flow diagram illustrating an embodiment of a process for a patient to release the patient's medical record to a third party.

FIG. 12 is a flow diagram 1200 illustrating an embodiment of a process for a patient to release the patient's medical record to a third party. In step 1210, the third party seeking the medical record of the patient is the user of the technology and uses a UMD to interact with the APS and the RPS. The role of the patient is different. The patient becomes the relying party in this situation. In one example, the patient's UMD has an App that allows it to operate in RPS mode. In step 1220, the patient's device is the RPS used to request the third-party user ID information from the UMD. The third party may be notified of the request via a display or some other user interface on the UMD and may give consent to release some or all of the requested user ID information via a user interface of the UMD. In step 1230, the UMD, having received consent from the third-party user specifying the release of some or all of the requested user ID information, may issue authorization of the release. In some embodiments, the authorization may take the form of a token, an electronic document, a digital file, or the like issued from the UMD to the RPS and then submitted by the RPS to the APS seeking verification of the token, electronic document, digital file, or the like via the secure network. In some other embodiments, the authorization may be a direct request from the RPS or a token sent from the UMD to the APS. This APS may be the same APS that issues the patient MIC to the patient or a different APS that issues the third-party MIC to the third-party user.

In step 1240, the RPS receives the released user ID information which is verified as being trusted user ID information. In different embodiments, the APS may receive the authorization from the UMD (e.g., direct request in FIG. 7 or token in FIG. 8) or examine the authorization from the RPS (e.g., electronic documents in FIGS. 5 and 6 or token in FIG. 8) for verification or nonverification. When the authorization is verified, it establishes that the user ID information received by the RPS is valid and can be trusted. In some embodiments, the RPS may receive and use a public key or some other electronic document or digital file to verify that the user ID information received from the UMD is trustworthy.

Next, the RPS uses the trusted user ID information, which may be received from the UMD or the APS, to verify the identity of the user making the request for the medical record using the UMD in step 1250. In some cases, the verification may involve matching the user's name and age. In other cases, more may be required to satisfy the RPS. For instance, the verification may involve matching other biographic and/or biometric information and/or additional information. If the identity of the user is not verified, the RPS may request resubmission of the user ID information from the UMD. In step 1260, when the identity of the user from the UMD is verified to the satisfaction of the RPS, the RPS may provide the entire medical record or a selective part of the medical record to the UMD.

The third-party user can be a nonhuman entity. In that case, the user ID information may include data such as employer or company identification number, address, company officers, etc.

In specific embodiments, the medical record obtained by the patient may be stored on a computer-readable storage medium such as a medical information card (or bracelet, chain, sleeve, etc.) or on a third-party storage medium such as a service provider storage. In emergency situations, medical personnel such as first responders can obtain the medical information of the patient quickly and reliably by reading the information from the medical information card carried by the patient or by accessing the information stored by the service provider. See, e.g., U.S. Patent Application Publication 2018/0166160, paragraphs [0024] to [0031] and FIGS. 1-8, the disclosure of which is incorporated herein by reference. The medical information can be securely accessed by medical personnel via advance authorization from the patient using an access code, key, or the like.

Figure 13:
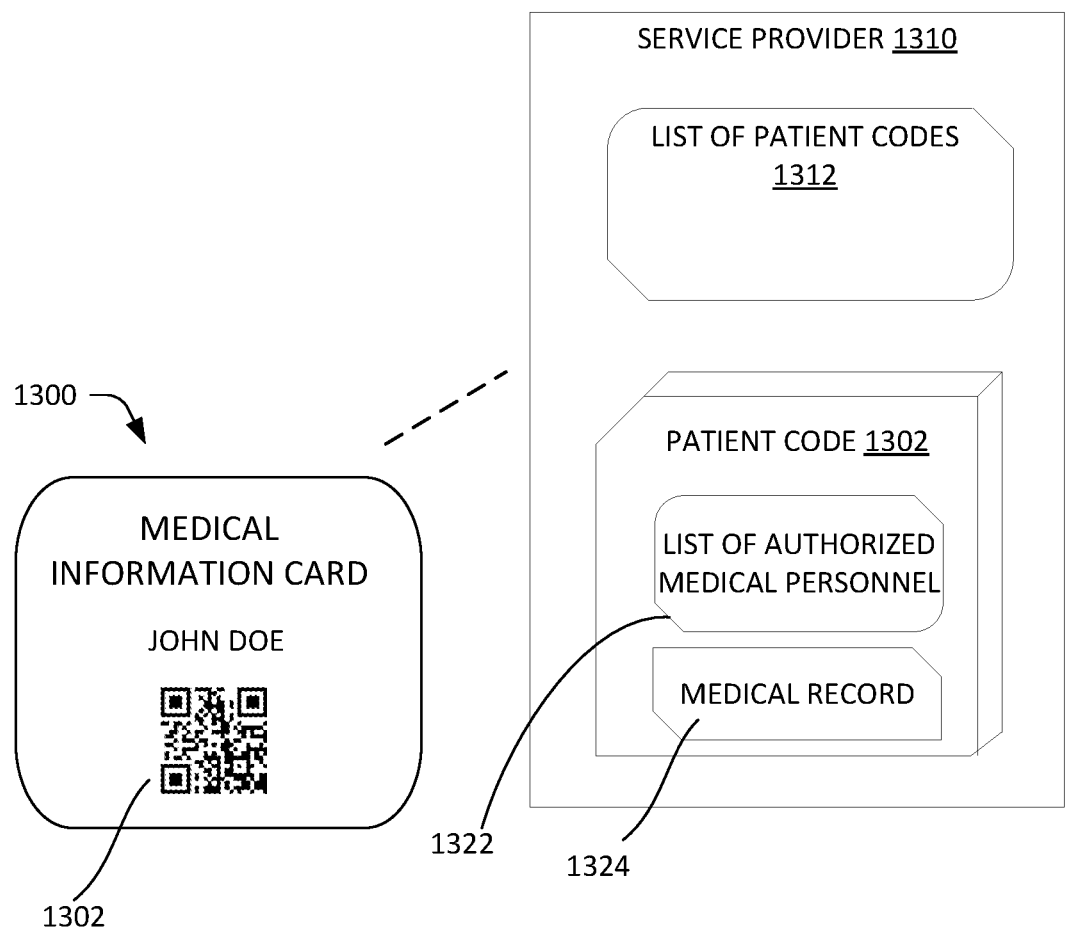
FIG. 13 shows an example of a medical information card and a service provider.

Alternatively, the medical information card may include a bar code or a QR code which uniquely identifies the patient. FIG. 13 shows an example of a medical information card 1300 having a unique patient code 1302. Also shown is a service provider 1310 storing a list of patient codes 1312 and, for each patient code, a list of authorized medical personnel 1322 and a medical record 1324.

Figure 14:
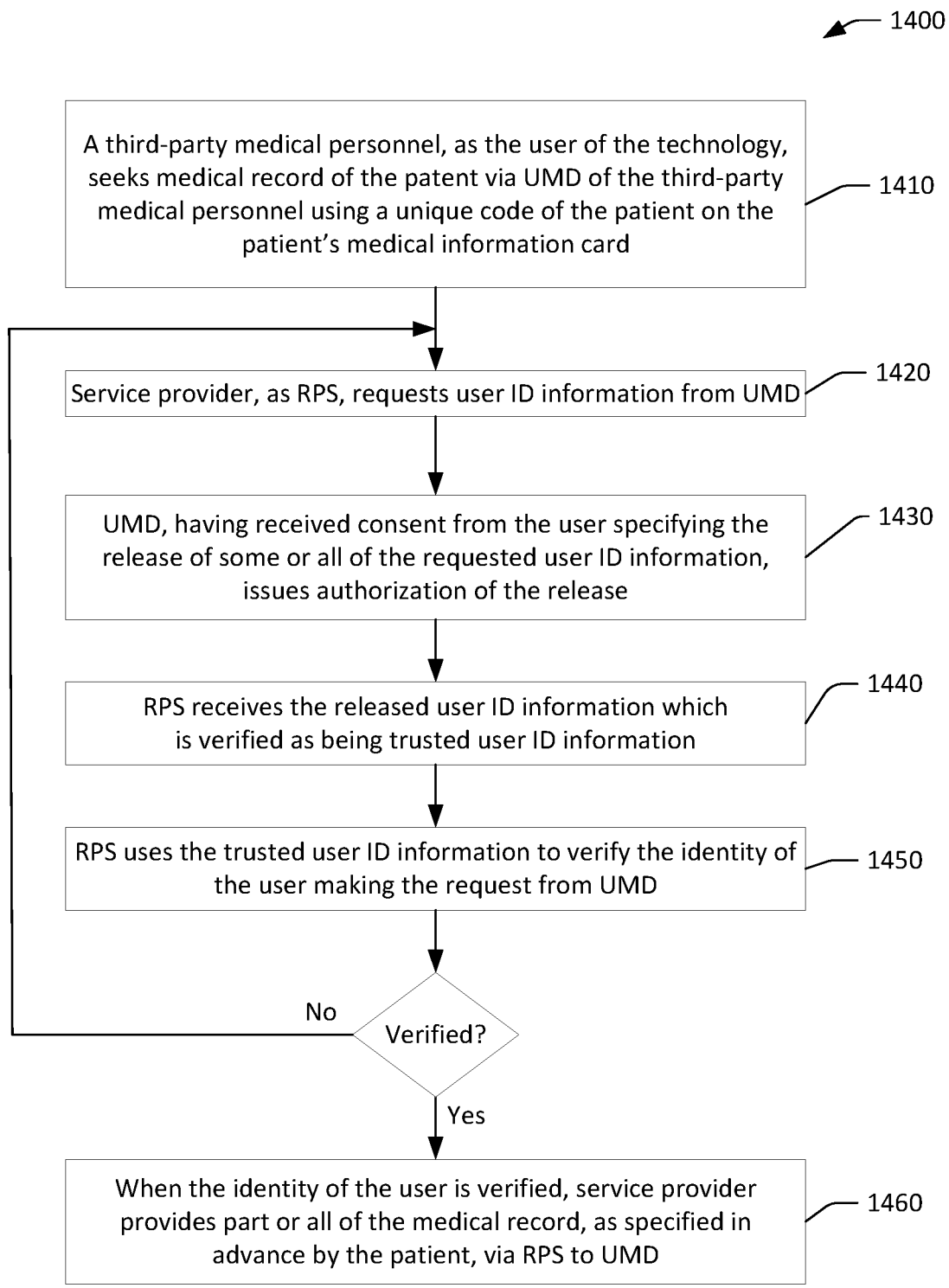
FIG. 14 is a flow diagram illustrating an embodiment of a process for medical personnel to request a patient's medical record stored by a service provider.

FIG. 14 is a flow diagram illustrating an embodiment of a process 1400 for medical personnel to request the patient's medical record stored by a service provider 1310. The medical personnel are referred to as third-party medical personnel that need not be affiliated with the medical office from which the patient obtained the medical record. A good example would be first responders. The patient can store his or her entire medical record or selectively store portions of the medical record with the service provider.

In step 1410, the third-party medical personnel may use a UMD to interact with the APS and the RPS (the service provider's system, also referred to as service provider system, service provider device, or service provider computer) and seek the medical record of the patient using the unique patient code obtained from the patient's medical information card 1300. The RPS compares the patient code 1302 received from the UMD against a list of patient codes 1312 corresponding to patients that have medical records 1324 stored at the service provider's system RPS. The process proceeds when there is a match; when there is not a match, the UMD may be notified and asked to obtain the proper patient code to proceed any further. In step 1420, the RPS requests the user ID information from the UMD. In step 1430, the UMD, having received consent from the medical personnel specifying the release of some or all of the requested user ID information, issues authorization of the release. In step 1440, the RPS receives the released user ID information which is verified as being trusted user ID information. When the authorization is verified, it establishes that the user ID information received by the RPS is valid and can be trusted. Next, the RPS uses the trusted user ID information, which may be received from the UMD or the APS, to verify the identity of the user making the request for the medical record using the UMD in step 1450. In some cases, the patient may provide in advance a list of authorized medical personnel 1322 that are authorized to access the patient's medical record stored by the service provider. The list can include specific names of individuals and medical organizations as well as general categories such as first responders. If the identity of the user is not verified, the RPS may request resubmission of the user ID information from the UMD. In step 1460, when the identity of the user from the UMD is verified to the satisfaction of the RPS, the RPS may provide the entire medical record or a selectively part of the medical record to the UMD. Again, the patient can specify in advance which medical personnel have access to which portion(s) of the medical record.

CONCLUSION

The inventive concepts taught by way of the examples discussed above are amenable to modification, rearrangement, and embodiment in several ways. For example, the concepts are applicable beyond the example of medical or health-related records; other, regulated situations that involve providing data or information to a user or involve accepting the same from a user are included. Examples include treatment record, driving record, training record, educational record, employment record, personnel record, travel record, membership record, tax record, bankruptcy record, court record, real estate record, business record, service record, credit history record, bank record, any type of private or public activity record, and the like. All these are within the scope of the present disclosure.

Accordingly, although the present disclosure has been described with reference to specific embodiments and examples, persons skilled in the art will recognize that changes may be made in form and detail without departing from the spirit and scope of the disclosure.

Certain attributes, functions, steps of methods, or sub-steps of methods described herein may be associated with physical structures or components, such as a module of a physical device that, in implementations in accordance with this disclosure, make use of instructions (e.g., computer executable instructions) that are embodied in hardware, such as an application specific integrated circuit, computer-readable instructions that cause a computer (e.g., a general-purpose computer) executing the instructions to have defined characteristics, a combination of hardware and software such as processor implementing firmware, software, and so forth so as to function as a special purpose computer with the ascribed characteristics. For example, in embodiments a module may comprise a functional hardware unit (such as a self-contained hardware or software or a combination thereof) designed to interface the other components of a system such as through use of an API. In embodiments, a module is structured to perform a function or set of functions, such as in accordance with a described algorithm. This disclosure may use nomenclature that associates a component or module with a function, purpose, step, or sub-step to identify the corresponding structure which, in instances, includes hardware and/or software that function for a specific purpose. For any computer-implemented embodiment, "means plus function" elements will use the term "means;" the terms "logic" and "module" and the like have the meaning ascribed to them above, if any, and are not to be construed as means.

The claims define the invention and form part of the specification. Limitations from the written description are not to be read into the claims.

An interpretation under 35 U.S.C. § 112(f) is desired only where this description and/or the claims use specific terminology historically recognized to invoke the benefit of interpretation, such as "means," and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features and/or methodological steps, it is to be understood that the subject matter defined in the appended claims is not necessarily limited to the specific features or steps described. Rather, the specific features and steps are disclosed as example forms of implementing the claimed subject matter. To the extent headings are used, they are provided for the convenience of the reader and are not to be taken as limiting or restricting the systems, techniques, approaches, methods, devices to those appearing in any section. Rather, the teachings and disclosures herein can be combined, rearranged, with other portions of this disclosure and the knowledge of one of ordinary skill in the art. It is the intention of this disclosure to encompass and include such variation. The indication of any elements or steps as "optional" does not indicate that all other or any other elements or steps are mandatory.

What is claimed is:

1. A method for a patient having a patient device to request a medical record of the patient from a medical office having a medical office system, the method comprising:
    receiving, by the medical office system from the patient device, a request for the medical record;
    sending, by the medical office system to the patient device, a request for identification information of the patient;
    receiving, by the medical office system, part or all of patient information associated with a first mobile identification credential (MIC) which the patient device received from a first authorizing party system (APS), the patient having consented to release the part or all of patient information to the medical office system, and the part or all of patient information having been verified by the first APS before the medical office system sends the request for identification information of the patient to the patient device, the first APS being a separate system from the medical office system;

using, by the medical office system, the verified part or all of patient information associated with the first MIC to verify or not verify the identity of the patient; and verifying the identity of the patient, by the medical office system, before granting the request to provide the medical record to the patient.

2. The method of claim 1, wherein receiving the verified part or all of patient information comprises:

receiving, by the medical office system from the patient device, a token specifying the part or all of patient information which the patient has consented to release to the medical office system;

sending, by the medical office system to the first APS, the received token, which is to be verified by the first APS with another token sent from the patient device to the first APS;

when the tokens are received by the first APS within a preset timeframe and are verified by the first APS, receiving, by the medical office system from the first APS, the verified part or all of patient information; and when the tokens are not received by the first APS within the preset timeframe or are not verified by the first APS, receiving, by the medical office system from the first APS, a notification to resubmit the request for identification information of the patient.

3. The method of claim 1, wherein receiving the verified part or all of patient information comprises:

receiving, by the medical office system from the patient device, an electronic document specifying the part or all of patient information which the patient has consented to release to the medical office system;

sending, by the medical office system to the first APS, the received electronic document;

when the received electronic document is verified by the first APS, receiving, by the medical office system from the first APS, the verified part or all of patient information; and when the received electronic document is not verified by the first APS, receiving, from the medical office system from the first APS, a notification to resubmit the request for identification information of the patient.

4. The method of claim 1, wherein receiving the verified part or all of patient information comprises:

receiving, by the medical office system from patient device, an electronic document and the part or all of patient information which the patient has consented to release to the medical office system;

sending, by the medical office system to the first APS, the received electronic document;

when the received electronic document is verified by the first APS, receiving, by the medical office system from the first APS, an authentication key to verify the part or all of patient information received from the patient device; and when the received electronic document is not verified by the first APS, receiving, by the medical office system from the first APS, a notification to resubmit the request for identification information of the patient.

5. The method of claim 1, wherein receiving the verified part or all of patient information comprises:

receiving, by the medical office system from the patient device, the part or all of patient information which the patient has consented to release to the medical office system; and receiving, by the medical office system from the first APS, an authentication key to verify the part or all of patient information received from the patient device, based on a request sent from the patient device to the first APS.

6. The method of claim 1, further comprising:

sending, by the medical office system to the patient device, a request for a liveness check;

receiving, (i) by the medical office system, from the patient, liveness check information and evaluating the liveness check information to determine whether the liveness check is valid or invalid, or (ii) by the medical office system, from the first APS which has evaluated liveness check information received from the patient, a determination by the first APS as to whether the liveness check is valid or invalid;

granting the request from the patient, by the medical office system, to provide the medical record to the patient when the identity of the patient is verified and when the liveness check is valid; and denying the request, by the medical office system, to provide the medical record to the patient when the identity of the patient is not verified or when the liveness check is invalid.

7. A medical office system for processing a request for a medical record from a patient device of a patient, the medical office system comprising a computer having a memory and a processor programmed to:

receive, from the patient device, a request for the medical record;

send, to the patient device, a request for identification information of the patient;

receive part or all of patient information associated with a first mobile identification credential (MIC) which the patient device received from a first authorizing party system (APS), the patient having consented to release the part or all of patient information to the medical office system, and the part or all of patient information having been verified by the first APS before the medical office system sends the request for identification information of the patient to the patient device, the first APS being a separate system from the medical office system;

use the verified part or all of patient information associated with the first MIC to verify or not verify the identity of the patient; and verify the identity of the patient before granting the request to provide the medical record to the patient.

8. The medical office system of claim 7, wherein receiving the verified part or all of patient information comprises:

receiving, by the medical office system from the patient device, a token specifying the part or all of patient information which the patient has consented to release to the medical office system;

sending, by the medical office system to the first APS, the received token, which is to be verified by the first APS with another token sent from the patient device to the first APS;

when the tokens are received by the first APS within a preset timeframe and are verified by the first APS, receiving, by the medical office system from the first APS, the verified part or all of patient information; and when the tokens are not received by the first APS within the preset timeframe or are not verified by the first APS, receiving, by the medical office system from the first APS, a notification to resubmit the request for identification information of the patient.

9. The medical office system of claim 7, wherein receiving the verified part or all of patient information comprises:
receiving, by the medical office system from the patient device, an electronic document specifying the part or all of patient information which the patient has consented to release to the medical office system;
sending, by the medical office system to the first APS, the received electronic document;
when the received electronic document is verified by the first APS, receiving, by the medical office system from the first APS, the verified part or all of patient information; and
when the received electronic document is not verified by the first APS, receiving, from the medical office system from the first APS, a notification to resubmit the request for identification information of the patient.

10. The medical office system of claim 7, wherein receiving the verified part or all of patient information comprises:
receiving, by the medical office system from patient device, an electronic document and the part or all of patient information which the patient has consented to release to the medical office system;
sending, by the medical office system to the first APS, the received electronic document;
when the received electronic document is verified by the first APS, receiving, by the medical office system from the first APS, an authentication key to verify the part or all of patient information received from the patient device; and
when the received electronic document is not verified by the first APS, receiving, by the medical office system from the first APS, a notification to resubmit the request for identification information of the patient.

11. The medical office system of claim 7, wherein receiving the verified part or all of patient information comprises:
receiving, by the medical office system from the patient device, the part or all of patient information which the patient has consented to release to the medical office system; and
receiving, by the medical office system from the first APS, an authentication key to verify the part or all of patient information received from the patient device, based on a request sent from the patient device to the first APS.

12. The medical office system of claim 7, wherein the computer is further programmed to:
send, by the medical office system to the patient device, a request for a liveness check;
receive, (i) by the medical office system, from the patient, liveness check information and evaluate the liveness check information to determine whether the liveness check is valid or invalid, or (ii) by the medical office system, from the first APS which has evaluated liveness check information received from the patient, a determination by the first APS as to whether the liveness check is valid or invalid;
grant the request from the patient, by the medical office system, to provide the medical record to the patient when the identity of the patient is verified and when the liveness check is valid; and
deny the request, by the medical office system, to provide the medical record to the patient when the identity of the patient is not verified or when the liveness check is invalid.

13. A system, comprising: a patient device and a medical office system of a medical office, for a patient using the patient device to request a medical record of the patient from the medical office system of the medical office, the medical office system including a medical office computer having a first memory and a first processor programmed to perform operations according to medical office instructions, the patient device including a patient computer having a second memory and a second processor programmed to perform operations according to patient instructions, the patient device having received a first mobile identification credential (MIC) from a first authorizing party system (APS), the first APS being a separate system from the medical office system, the first APS including an APS computer having a third memory and a third processor programmed to perform operations according to APS instructions,
the patient device sending, to the medical office system, a request for providing the medical record to the patient;
the medical office system sending, to the patient device, a request for identification information of the patient;
the patient device receiving, from the patient, consent to release part or all of patient information associated with the first MIC, the first APS having verified the part or all of patient information associated with the first MIC before the medical office system sends the request for identification information of the patient to the patient device;
(i) the patient device sending, to the medical office system, the consented part or all of patient information or (ii) the first APS sending, to the medical office system, the consented part or all of patient information as verified part or all of patient information associated with the first MIC;
the medical office system using the verified part or all of patient information associated with the first MIC to verify or not verify the identity of the patient; and
the medical office system verifying the identity of the patient before granting the request to provide the medical record to the patient.

14. The system of claim 13,
wherein the patient device sends, to the medical office system, a token specifying the part or all of patient information which the patient has consented to release to the medical office system;
wherein the medical office system sends, to the first APS, the received token;
wherein the patient device sends another token to the first APS;
wherein when the tokens are received by the first APS within a preset timeframe and are verified by the first APS, the medical office system receives the verified part or all of patient information; and
wherein when the tokens are not received by the first APS within the preset timeframe or are not verified by the first APS, the first APS sends, to the medical office system, a notification to resubmit the request for identification information of the patient.

15. The system of claim 13, further comprising:
a third-party system including a third-party computer having a fourth memory and a fourth processor programmed to perform operations according to third-party instructions,
wherein the third-party system sends, to the patient device, a request for the medical record of the patient;
wherein the patient device sends, to the third-party system, a request for identification information of the third party;
wherein the patient device receives part or all of third-party information associated with a second MIC which the third-party system received from the first APS or a second APS, wherein the third party has consented to release the part or all of third-party information to the patient device, and wherein the part or all of third-party information has been verified;

wherein the patient device uses the verified part or all of third-party information associated with the second MIC to verify or not verify the identity of the third party; and wherein the patient device verifies the identity of the third party before granting the third-party system the request to provide to the third party, part or all of the medical record as selected by the patient.

16. A system, comprising a medical personnel system and a service provider system of a service provider, for medical personnel using the medical personnel system to request a medical record of a patient from the service provider system of the service provider, the service provider system including a service provider computer having a first memory and a first processor programmed to perform operations according to service provider instructions, the medical personnel system including a medical personnel computer having a second memory and a second processor programmed to perform operations according to medical personnel instructions, the medical personnel computer having received a first mobile identification credential (MIC) from a first authorizing party system (APS), the first APS being a separate system from the service provider system, the first APS including an APS computer having a third memory and a third processor programmed to perform operations according to APS instructions, the medical personnel system sending, to the service provider system, a request for providing the medical record of the patient to the medical personnel;

the service provider system sending, to the medical personnel system, a request for identification information of the medical personnel;

the medical personnel system receiving, from the medical personnel, consent to release part or all of medical personnel information associated with the first MIC, the first APS having verified the part or all of patient information associated with the first MIC before the medical personnel system sends the request for identification information of the patient to the medical personnel system;

(i) the medical personnel system sending, to the service provider system, the consented part or all of medical personnel information or (ii) the first APS sending, to the service provider system, the consented part or all of medical personnel information as verified part or all of medical personnel information associated with the first MIC;

the service provider system using the verified part or all of medical personnel information associated with the first MIC to verify or not verify the identity of the medical personnel; and the service provider system verifying the identity of the medical personnel before granting the request to provide the medical record of the patient to the medical personnel.

17. The system of claim 16, wherein the service provider system reviews a list of authorized medical personnel which the patient has provided to the service provider in advance to have access to the medical record of the patient, and matches the medical personnel of the medical personnel system with an entry on the list of authorized medical personnel, before granting the request to provide the medical record of the patient to the medical personnel.

18. The system of claim 16, wherein the medical personnel system provides, to the service provider system, a patient code obtained from a medical information card of the patient;

wherein the service provider system compares the received patient code against a list of patient codes; and wherein the service provider system grants the medical personnel system the request to provide the part or all of the medical record when the service provider system verifies the identity of the medical personnel and matches the received patient code with a patient code of the patient having the medical record stored by the service provider system.

19. The system of claim 16, wherein the medical personnel system sends, to the service provider system, a token specifying the part or all of medical personnel information which the medical personnel have consented to release to the service provider system;

wherein the service provider system sends, to the first APS, the received token;

wherein the system sends another token to the first APS;

wherein when the tokens are received by the first APS within a preset timeframe and are verified by the first APS, the service provider system receives the verified part or all of medical personnel information; and wherein when the tokens are not received by the first APS within the preset timeframe or are not verified by the first APS, the first APS sends, to the service provider system, a notification to resubmit the request for identification information of the medical personnel.

20. The system of claim 15, wherein the first APS or the second APS verified the part or all of third-party information associated with the second MIC before the patient device sends the request for identification information of the third party to the third-party system.

21. The method of claim 1, wherein the first APS is a system of an official agency which verifies the part or all of patient information based on official records of the patient before the medical office system sends the request for identification information of the patient to the patient device.

22. The method of claim 21, wherein the first MIC comprises a first mobile driver's license issued by a Department of Motor Vehicles system as the first APS or a first mobile passport issued by a national agency system as the first APS.

* * * * *